US012699286B2

(12) United States Patent
Hart et al.

(10) Patent No.: US 12,699,286 B2
(45) Date of Patent: Aug. 4, 2026

(54) AUGMENTED REALITY GLASSES WITH OBJECT RECOGNITION USING ARTIFICAL INTELLIGENCE

(71) Applicants: William Hart, Aptos, CA (US); Edmond Arthur DeFrank, Northridge, CA (US); Nicolas DeFrank, Northridge, CA (US); Antonio DeFrank, Northridge, CA (US); Allen Mark Jones, Imperial Beach, CA (US)

(72) Inventors: William Hart, Aptos, CA (US); Edmond Arthur DeFrank, Northridge, CA (US); Nicolas DeFrank, Northridge, CA (US); Antonio DeFrank, Northridge, CA (US); Allen Mark Jones, Imperial Beach, CA (US)

( * ) Notice: Subject to any disclaimer, the term of this patent is extended or adjusted under 35 U.S.C. 154(b) by 0 days.

(21) Appl. No.: 19/234,254

(22) Filed: Jun. 10, 2025

(65) Prior Publication Data

US 2025/0306403 A1      Oct. 2, 2025

Related U.S. Application Data

(63) Continuation-in-part of application No. 18/406,160, filed on Jan. 7, 2024, now Pat. No. 12,326,616, which (Continued)

(51) Int. Cl.
*G02C 11/00*          (2006.01)
*A61B 3/11*          (2006.01)
(Continued)

(52) U.S. Cl.
CPC .............. *G02C 11/10* (2013.01); *A61B 3/112* (2013.01); *A61B 3/14* (2013.01); *G02C 7/04* (2013.01); *A61B 3/12* (2013.01); *A61B 5/18* (2013.01)

(58) Field of Classification Search
CPC .......... G02C 11/10; G02C 7/04; G02C 7/086; A61B 3/112; A61B 3/14; A61B 3/12; A61B 5/18
(Continued)

(56) References Cited

U.S. PATENT DOCUMENTS

2012/0242697  A1*   9/2012   Border ................. G02B 27/017
                                                          345/633
2015/0220157  A1*   8/2015   Marggraff ............. G06F 3/0485
                                                          345/156

(Continued)

*Primary Examiner* — Bumsuk Won
*Assistant Examiner* — Rahman Abdur
(74) *Attorney, Agent, or Firm* — Edmond DeFrank

(57) ABSTRACT

The embodiment disclose a wearable augmented reality eyewear system including a frame supporting left and right transparent lenses. A plurality of outward-facing cameras mounted on the frame have overlapping fields of view for capturing real-time images of the environment. A plurality of inward-facing cameras integrated in the frame or lenses detect pupil size, pupil dilation, and gaze direction using infrared imaging. A digital processor analyzes gaze direction and fixation based on virtual grid coordinates, initiates an object or person recognition routine using images from the outward-facing cameras, and compares detected features with records in a database. At least one lens includes an AR projection system embedded therein and configured to superimpose data about the recognized object or person in the user's field of view. An audio speaker positioned near the user's ear outputs related audio. A wireless communication module enables real-time data exchange with a cloud-based platform.

20 Claims, 21 Drawing Sheets

Related U.S. Application Data is a continuation of application No. 17/829,226, filed on May 31, 2022, now Pat. No. 11,880,091, which is a continuation of application No. 17/083,961, filed on Oct. 29, 2020, now Pat. No. 11,347,084, which is a continuation of application No. 15/643,673, filed on Jul. 7, 2017, now abandoned, which is a continuation of application No. 14/881,921, filed on Oct. 13, 2015, now Pat. No. 9,720,259.

(60) Provisional application No. 62/063,194, filed on Oct. 13, 2014.

(51) Int. Cl.
*A61B 3/14* (2006.01)
*G02C 7/04* (2006.01)
*A61B 3/12* (2006.01)
*A61B 5/18* (2006.01)

(58) Field of Classification Search
USPC ......................................................... 351/206
See application file for complete search history.

(56) References Cited

U.S. PATENT DOCUMENTS

| | | | |
|---|---|---|---|
| 2016/0071423 A1* | 3/2016 | Sales ................... | A61B 5/0022 434/127 |
| 2016/0078278 A1* | 3/2016 | Moore ................. | G02B 27/017 345/8 |

* cited by examiner

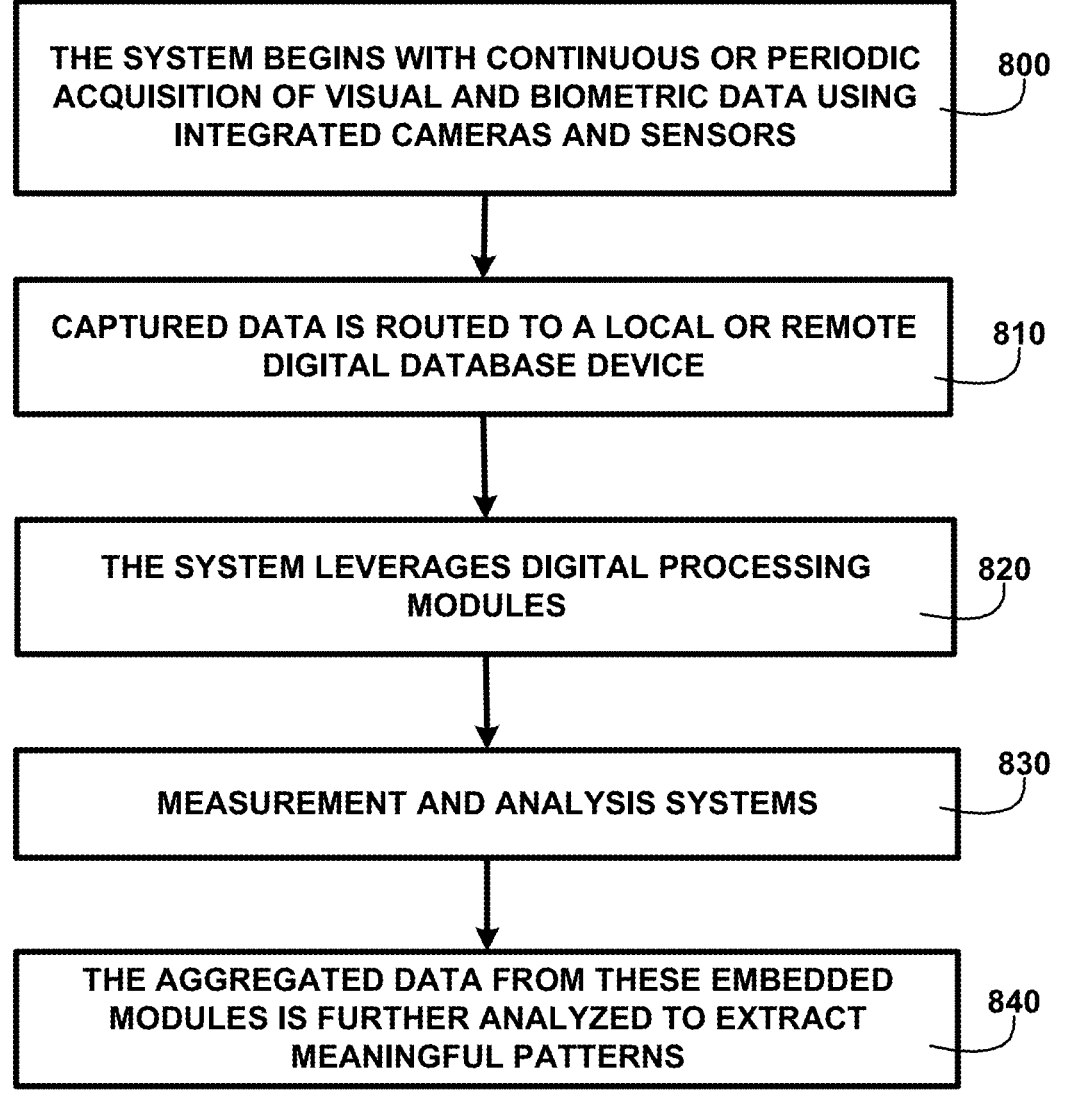

THE SYSTEM BEGINS WITH CONTINUOUS OR PERIODIC ACQUISITION OF VISUAL AND BIOMETRIC DATA USING INTEGRATED CAMERAS AND SENSORS — 800

CAPTURED DATA IS ROUTED TO A LOCAL OR REMOTE DIGITAL DATABASE DEVICE — 810

THE SYSTEM LEVERAGES DIGITAL PROCESSING MODULES — 820

MEASUREMENT AND ANALYSIS SYSTEMS — 830

THE AGGREGATED DATA FROM THESE EMBEDDED MODULES IS FURTHER ANALYZED TO EXTRACT MEANINGFUL PATTERNS — 840

FIG. 8

YOU HAVE A MEETING @ 2PM

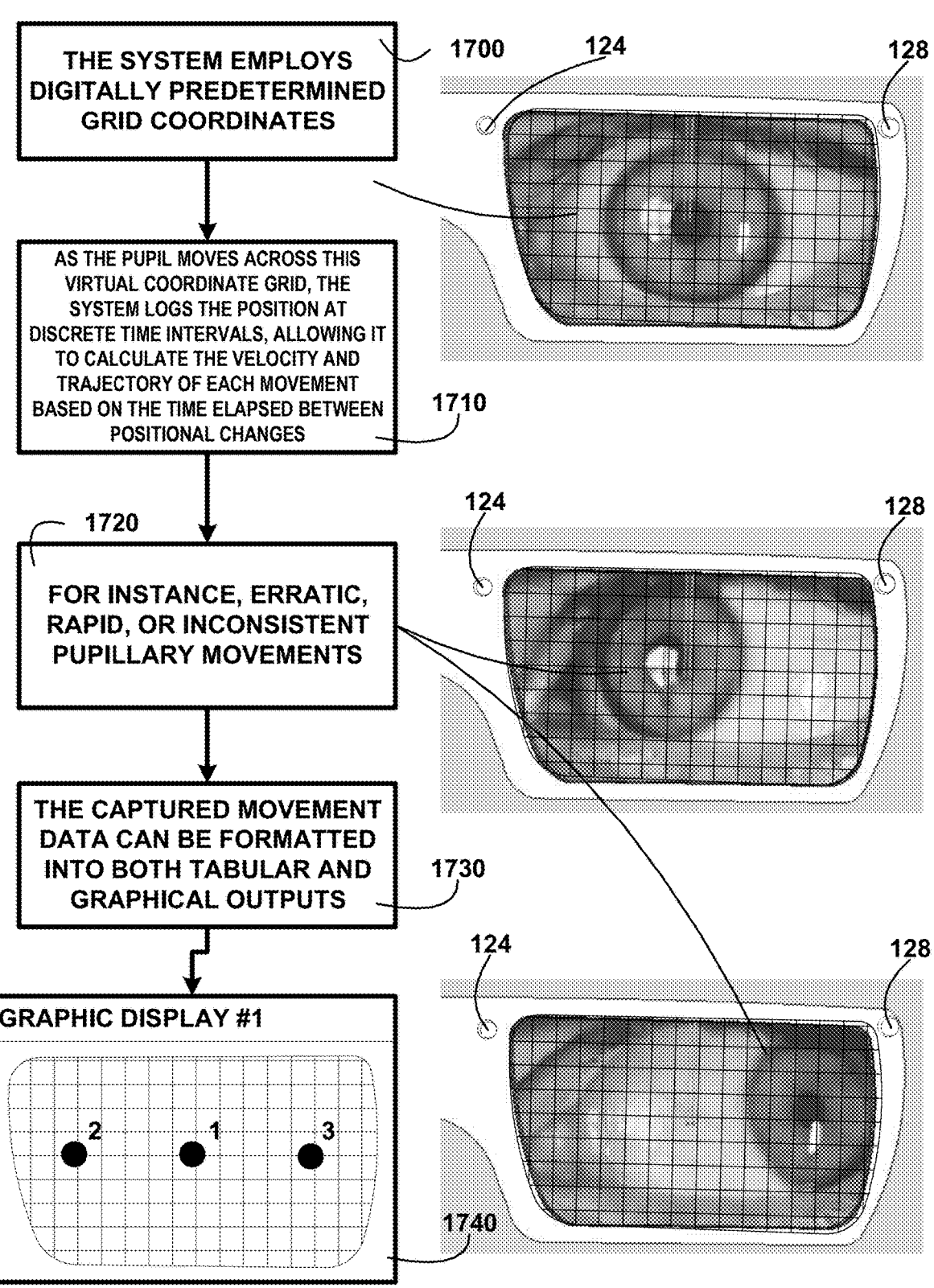

THE SYSTEM EMPLOYS DIGITALLY PREDETERMINED GRID COORDINATES

1700

124

128

AS THE PUPIL MOVES ACROSS THIS VIRTUAL COORDINATE GRID, THE SYSTEM LOGS THE POSITION AT DISCRETE TIME INTERVALS, ALLOWING IT TO CALCULATE THE VELOCITY AND TRAJECTORY OF EACH MOVEMENT BASED ON THE TIME ELAPSED BETWEEN POSITIONAL CHANGES

1710

1720

FOR INSTANCE, ERRATIC, RAPID, OR INCONSISTENT PUPILLARY MOVEMENTS

124

128

THE CAPTURED MOVEMENT DATA CAN BE FORMATTED INTO BOTH TABULAR AND GRAPHICAL OUTPUTS

1730

GRAPHIC DISPLAY #1

1900
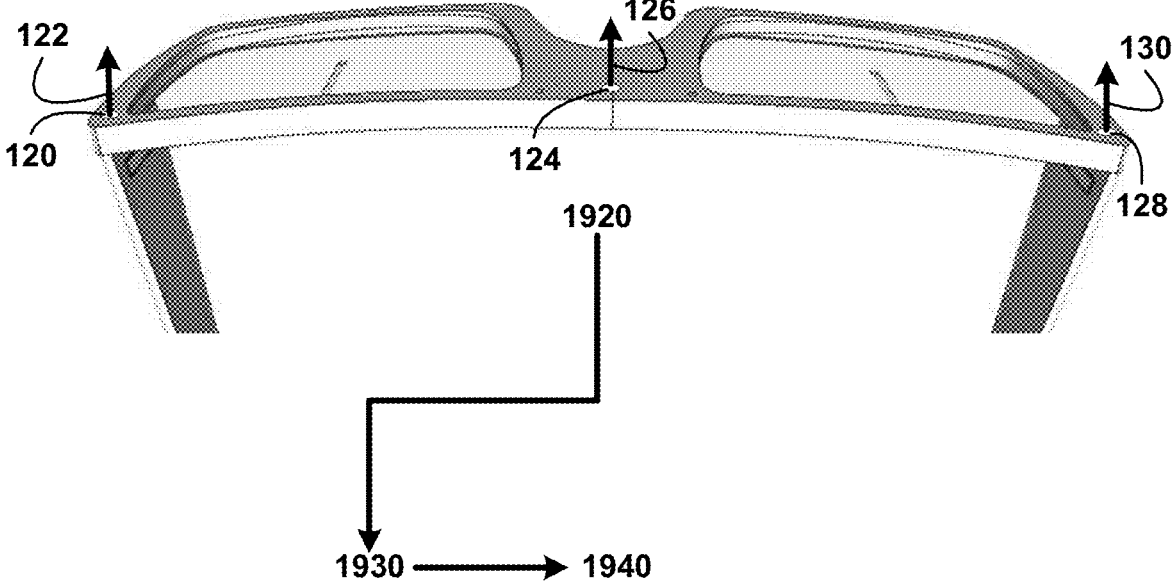
122
126
130
120
124
128
1920
1930 ⟶ 1940
FIG. 19

AUGMENTED REALITY GLASSES WITH OBJECT RECOGNITION USING ARTIFICAL INTELLIGENCE

CROSS-REFERENCE TO RELATED APPLICATIONS

This patent application is a continuation-in-part of and claims priority to United States patent application entitled: "PUPILLARY RESPONSE FEEDBACK EYEWEAR", U.S. Ser. No. 18/406,160 filed on Jan. 7, 2024 filed by William Hart, which is a Continuation and claims priority to United States patent application entitled: "PUPILLARY RESPONSE FEEDBACK EYEWEAR", U.S. Ser. No. 17/829,226 filed on May 31, 2022 filed by William Hart, which is a Continuation and claims priority of United States patent application entitled: PUPILLARY RESPONSE FEEDBACK EYEWEAR", U.S. Ser. No. 17/083,961 filed on Oct. 29, 2020 filed by William Hart, U.S. Pat. No. 11,347,084 Issued May 31, 2022, which is a Continuation and claims priority of United States patent application entitled: "PUPILLARY RESPONSE FEEDBACK EYE-WEAR", U.S. Ser. No. 15/643,673 filed on Jul. 7, 2017 filed by William Hart, which is a Continuation and claims priority of United States patent application entitled: "EYEWEAR PUPILOMETER", U.S. Ser. No. 14/881,921 filed on Oct. 13, 2015 filed by William Hart, U.S. Pat. No. 9,720,259 Issued Aug. 1, 2017, which is a Continuation and claims priority of United States Provisional patent application entitled: "EYEWEAR PUPILOMETER", U.S. Ser. No. 62/063,194 filed on Oct. 13, 2014 filed by William Hart, all being incorporated herein by reference.

BACKGROUND

Eyewear is generally considered to only deal with optical issues. However modern technology has expanded people's needs and reliance on digital information. Cell phones, smartphones, and tablets require manual holding and carrying. These devices also need digits (fingers) to operate effectively. There are situations where a person may have difficulty in even answering a phone call, for example, carrying groceries, or young children.

BRIEF DESCRIPTION OF THE DRAWINGS

FIG. 8 shows a block diagram of an overview flow chart of smart eyewear glasses modules and systems of one embodiment.

FIG. 17 shows for illustrative purposes only an example of pupillary movement tracking of one embodiment.

FIG. 19 shows for illustrative purposes only an example of AI response with AR imagery of one embodiment.

SUMMARY OF THE INVENTION

Figure 1:
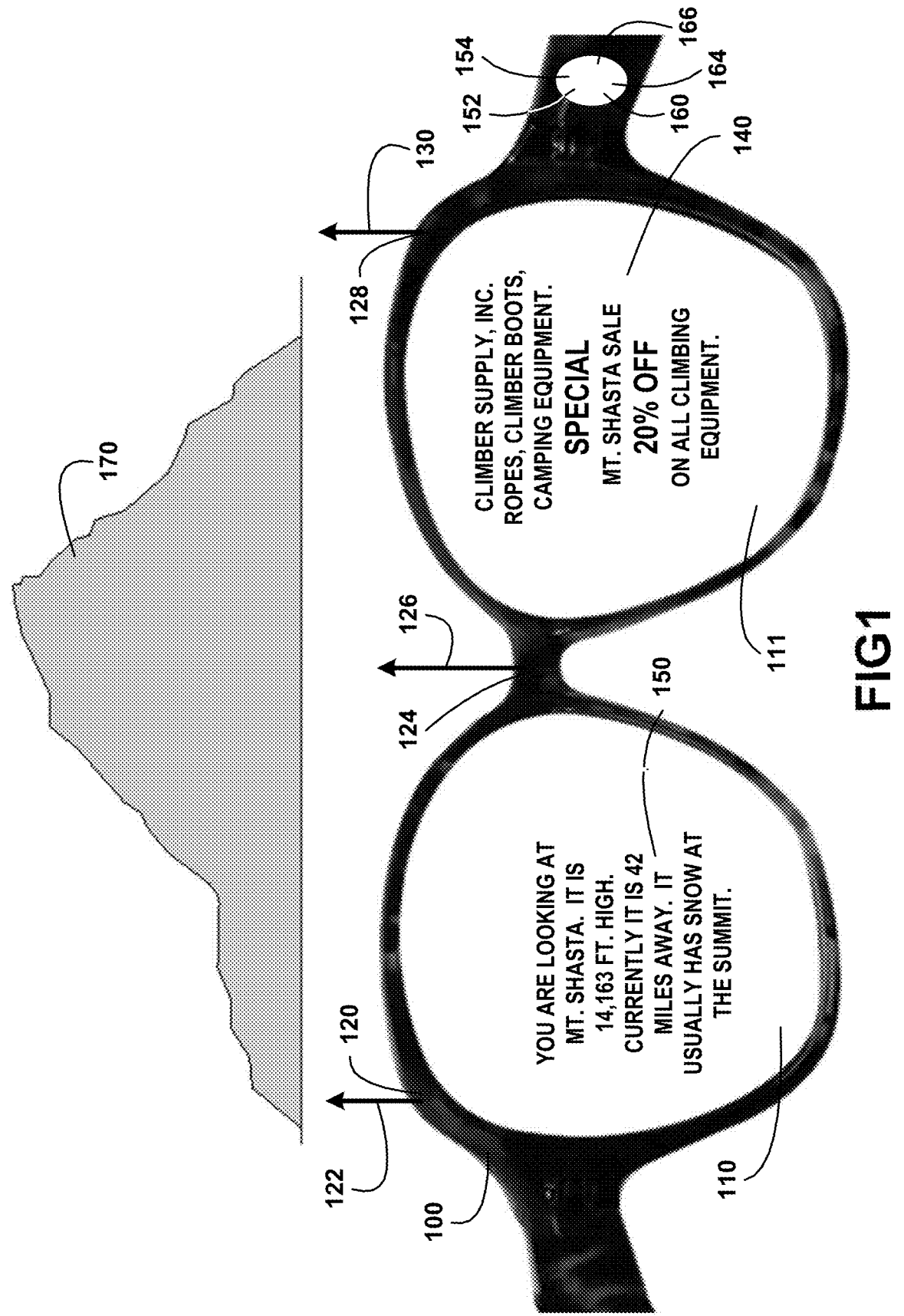
FIG. 1 shows for illustrative purposes only an example of a user wearing and interacting with smart eyewear glasses of one embodiment.

The present invention relates to wearable systems that combine real-time biometric sensing, environmental perception, and contextual data augmentation within a transparent visual interface. More specifically, the invention describes a system that integrates inward-facing optical sensors for monitoring a user's ocular behavior, such as pupil size, gaze direction, and fixation patterns, with outward-facing imaging systems that capture the user's surrounding environment. These systems work in concert to provide gaze-responsive augmented reality (AR) overlays directly within the user's visual field.

The inward-facing sensors, which can be an image capture device, an infrared camera, or imaging modules or the like that continuously track eye metrics to generate a precise gaze vector. This vector is mapped against a virtual coordinate grid that corresponds to the user's field of view through the display surface. When the user fixates on a particular area for a defined duration, the system interprets this as intentional engagement. In response, the outward-facing sensors isolate and analyze the corresponding region of the environment using object, scene, or facial recognition algorithms. The system then retrieves contextually relevant information, such as object identity, metadata, or user history, and superimposes that information into the appropriate location on the transparent lens surface, synchronized to the user's gaze.

The invention further provides real-time visual and audio feedback, enabling the system to function as an intuitive, hands-free interface. This gaze-activated architecture allows for seamless navigation, information retrieval, and contextual interaction with both digital and physical content, without requiring physical gestures or voice commands. The system architecture supports dynamic overlays that adapt based on the user's visual attention, physical environment, and application context, enabling advanced use cases in navigation, social recognition, training, accessibility, and cognitive diagnostics.

By fusing biometric inputs with real-time environmental perception and AR projection, the invention enables an intelligent, gaze-responsive interface that bridges human attention with contextual computing. This system architecture predates and anticipates the convergence of wearable eye-tracking hardware, scene-understanding vision modules, and gaze-triggered AR content delivery.

In the following description, reference is made to the accompanying drawings, which form a part hereof, and which are shown by way of illustration a specific example in which the invention may be practiced. It is to be understood that other embodiments may be utilized and structural changes may be made without departing from the scope of the embodiments. It should be noted that the descriptions that follow, for example, in terms of computer graphics processing for selective visual display systems in AI-enhanced augmented reality glasses are described for illustrative purposes and the underlying system can apply to any number and multiple types of vision eyewear. In one embodiment, computer graphics processing for selective visual display systems in AI-enhanced augmented reality glasses can be configured using optical fibers to communicate images. The computer graphics processing for selective visual display systems in AI-enhanced augmented reality glasses can be configured to include pupil movement and size in visible light and can be configured to include pupil movement and size in infrared wavelengths using the present invention. The references herein to the computer graphics processing for selective visual display systems in AI-enhanced augmented reality glasses may include computer graphics display augmented reality eyeglasses and smart eyewear glasses interchangeably without any change in meaning.

FIG. 1 illustrates an augmented reality (AR) eyewear system 100 worn by a user. The system includes a set of outward-facing cameras 120, 124, and 128 integrated across the frame, providing overlapping fields of view for real-time environmental capture. As the user visually fixates on a real-world object 170, such as a landmark or storefront, within the composite field of view, the system detects gaze fixation using inward-facing infrared eye-tracking cameras and a lens-embedded virtual coordinate grid. Upon confirming fixation above a programmable threshold duration (e.g., 500 ms), the system initiates object recognition and retrieves contextual data using an artificial intelligence (AI) module linked to a remote server 160. Augmented information related to the object (e.g., "Mt. Shasta, Elevation 14, 163 ft., 22 miles away") is then projected onto the interior surface of the left lens 110 via an embedded projection system. Simultaneously, commercial data (e.g., nearby outfitter promotions) may be projected on the right lens 111 and optionally vocalized via a frame-integrated speaker for discrete audio delivery. This configuration allows hands-free, gaze-triggered access to relevant environmental, commercial, or navigational data without requiring user interaction via touch, voice, or physical gestures.

In one embodiment, the system projects contextual information onto the interior surface of the left lens 110. For example, when the user fixates on a distant landmark such as a mountain peak, the system retrieves geospatial and descriptive metadata through cloud-based query services. The resulting augmented overlay may include text such as: "You are looking at Mt. Shasta. It is 14, 163 feet high. It is currently 22 miles away. Snow is typically present at the summit." 150 Concurrently, the right lens 111 may display a commercial advertisement generated in response to the recognized landmark, for example: "Climber Supply, Inc.— ropes, boots, camping gear—Mt. Shasta Sale: 20 percent off all climbing equipment." 140

The outward imaging subsystem includes at least a left side camera 120 with a corresponding field of view 122, a right-side camera 128 with overlapping field of view 130, and a centrally mounted camera 124 providing additional coverage of the environment in field 126. Upon detecting user gaze directed at the landmark, the system activates an artificial intelligence search module that queries relevant databases and commercial registries. In this instance, the system identifies a nearby retail supplier and projects additional augmented content on the right lens 111, such as: "Climber Supply, Inc.—3 miles ahead on the right at 123 Shasta Drive."

In addition to visual overlays, the system optionally includes text-to-speech conversion functionality. When activated, the relevant audio content associated with the visual display, such as advertisement text or landmark descriptions, is vocalized to the user via a directional speaker embedded in the eyewear frame. The speaker is positioned in proximity to the user's ear to ensure privacy and clarity without requiring external headphones or devices.

The augmented reality eyewear system described herein enables enhanced environmental perception by combining real time visual capture with spatially anchored, gaze triggered overlays. The system supports high bandwidth human computer interaction through hands free visual and auditory augmentation of objects detected in the user's field of view. As the user surveys the environment, outward facing cameras capture live imagery, and inward facing sensors determine gaze fixation. The processing subsystem then resolves the user's point of interest, retrieves contextual or commercial data, and projects such information directly onto the lens surface in alignment with the identified object. This allows users to access detailed environmental information—including distances, names, historical context, or commercial offerings—without requiring touch or voice activation. The system thus functions as a dynamic, context aware visual interface enhancing both informational access and situational awareness.

The augmented reality eyewear system operates in conjunction with a distributed computing platform that includes a plurality of remote servers 154, a primary remote computing node 152, and one or more associated databases 162 configured to store captured image data, metadata, and recognition model outputs. An artificial intelligence module 164 residing on the remote computing node 152 performs real time analysis on scene data captured by the outward facing cameras. Specifically, when an object or feature is identified based on user gaze fixation, the image is transmitted to the remote platform, where the artificial intelligence module 164 executes recognition algorithms and queries the database 162 for matching entries. If a correlation is found, the relevant contextual metadata is returned to the eyewear system for visual rendering. A graphics processing unit 166, either embedded locally within the eyewear or housed within the remote platform, is responsible for rendering visual elements including static overlays, animated sequences, and augmented environmental annotations for projection on the user's display surface.

The system further comprises an augmented reality application 180 that resides on the remote platform and is responsible for assembling and formatting display content for delivery to the eyewear display subsystem. The application 180 processes text, icons, visual annotations, and multimedia content derived from database queries or real time image analysis. Textual data is routed to a projection control module, while graphical and multimedia elements are sent to a rendering engine that integrates these elements into a cohesive augmented display. A visual output system 182 embedded within the eyewear is configured to project this content onto at least one lens surface, aligned to the user's field of view and point of attention. The projection is managed by a real time display system 178 capable of rendering dynamic three dimensional environments, directional overlays, or layered visual effects that adapt to environmental context. Communication with the remote computing platform is maintained via a multimodal communication module 172 that supports wireless protocols including WiFi, cellular, and satellite links. This ensures continuous synchronization of data, augmented content, and artificial intelligence processing relative to the user's physical location and point of gaze.

Figure 2:
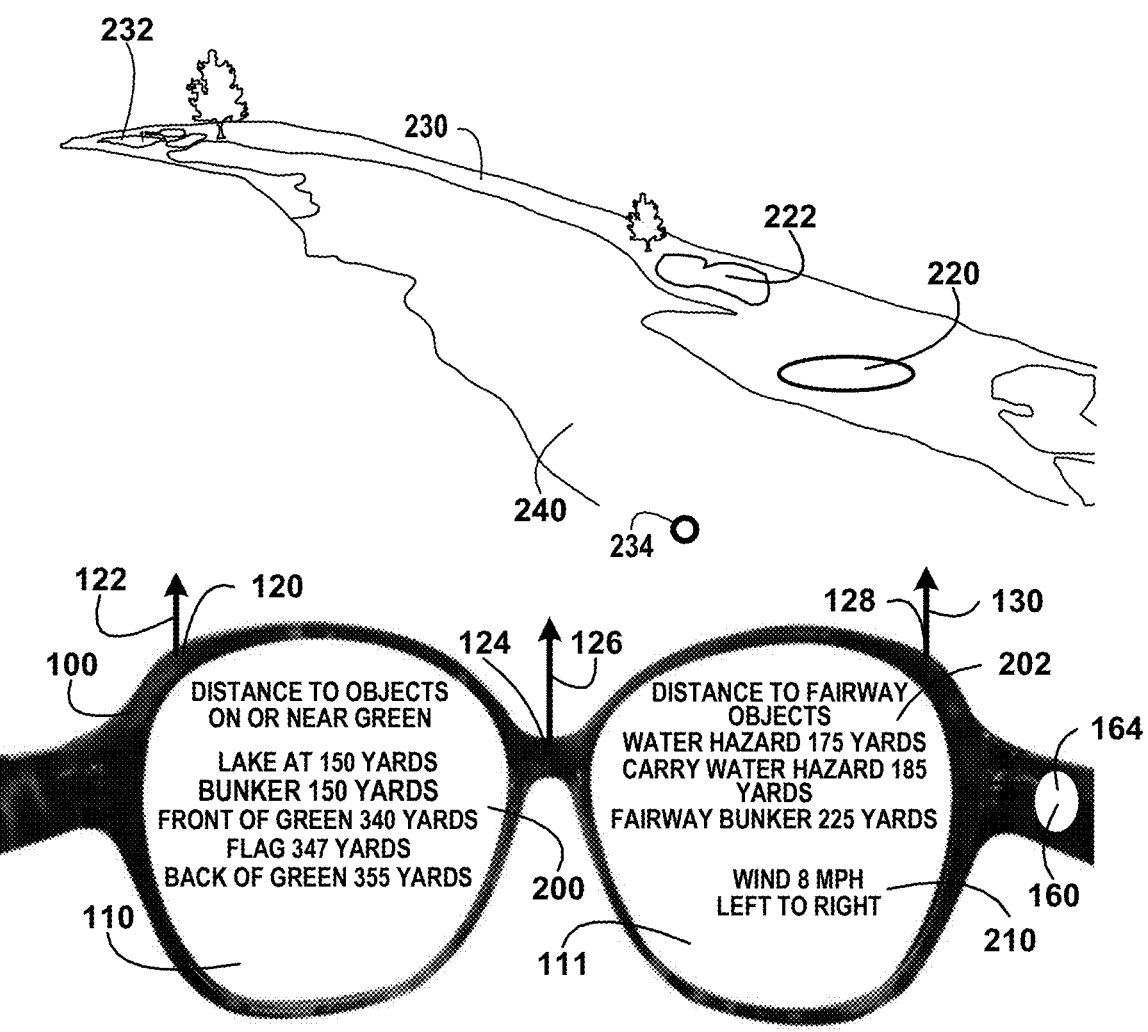
FIG. 2 shows for illustrative purposes only an example of smart eyewear glasses distance triangulation of one embodiment.

FIG. 2 illustrates an embodiment of the augmented reality eyewear system 100 configured to calculate real time distances to environmental features using binocular triangulation. The user, wearing the eyewear, is shown observing a field of view 200 encompassing a golf course fairway 240 extending from a tee box 234 to a hole location 232 on the putting green. The eyewear frame supports three outward facing cameras: a left side camera 120 with field of view 122, a right-side camera 128 with overlapping field of view 130, and a center mounted camera 124 with intermediate field of view 126. This multi angle camera array enables the system to generate stereoscopic image data, from which depth and distance can be computed via triangulation based on known camera baselines and angular field relationships analyzed using an artificial intelligence (AI) module 164 linked to a remote server 160. As the user scans the environment, the cameras capture images from slightly offset positions, allowing the processor to determine the spatial coordinates of visual targets located within the binocular overlap zone. In this example, the user directs attention toward the green, initiating distance analysis for specific points of interest.

Visual overlays projected onto the left lens 110 display computed distances to key elements around the green, including a front-side bunker at 320 yards, the front edge of the green at 340 yards, the flagstick at 347 yards, and the back edge of the green at 355 yards. Concurrently, the right lens 111 displays distances to objects along the approach path, including a water hazard 220 at 150 yards, a carry distance over the hazard at 185 yards, a fairway bunker 222 at 225 yards, and an out-of-bounds boundary line 230. Additional real time telemetry is projected onto the lens, such as wind speed and direction, which in this case is 8 miles per hour from left to right 210. The triangulated distances are calculated by analyzing the angular separation between the three camera fields of view and applying stereo disparity metrics to generate accurate object range estimates. The augmented reality system superimposes the computed distances and environmental conditions adjacent to the corresponding features in the user's line of sight, enabling context aware decision making without manual range finding devices.

In one embodiment illustrated in FIG. 2, the outward-facing cameras 120, 124, and 128 of the smart eyewear glasses 100 provide overlapping fields of view 122, 126, and 130, enabling stereo image capture for triangulating the position and distance to environmental features within the user's binocular field of vision 200. This triangulated distance data may be processed by a digital processor and projected onto the lens 110 or 111 using an AR module. In one embodiment as an example use case, when the user is engaged in a golfing activity, the eyewear may display superimposed distance indicators to various course features such as water hazards 220, bunkers 222, and flagsticks 232. Environmental data, including wind speed and direction 210, may also be captured via embedded sensors or retrieved via wireless communication modules to enhance situational awareness for the user. The integration of real-time environmental analysis and triangulation enhances the utility of the eyewear in outdoor sports where spatial judgment is critical.

Figure 3:
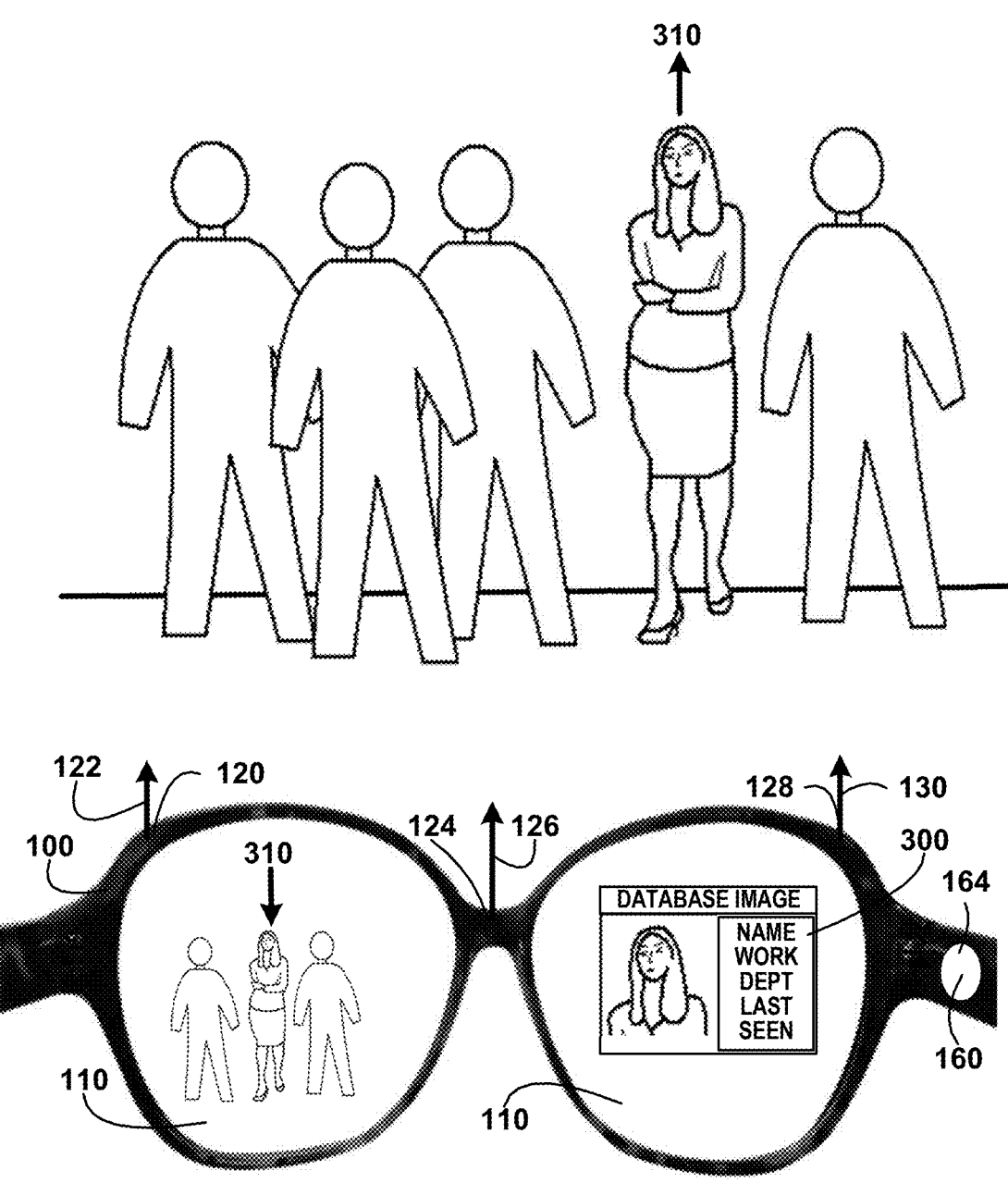
FIG. 3 shows for illustrative purposes only an example of smart eyewear glasses identifying a user's personal contact in a crowd of one embodiment.

FIG. 3 illustrates an embodiment of the augmented reality eyewear system 100 operating in a crowded environment where multiple individuals are present. The user, wearing eyewear system 100, views a broad scene using their natural binocular field of vision. The system includes three outward-facing cameras: a left-side camera 120, a center-mounted camera 124, and a right-side camera 128. These cameras collectively capture synchronized visual input across overlapping fields of view 122, 126, and 130, respectively.

When the user directs their gaze toward a particular sector of the crowd, the system detects gaze fixation using inward-facing sensors. In response, it captures high-resolution images from the outward-facing cameras 120, 124, and 128. If the user fixates on a specific individual-designated as reference subject 310—the system interprets this behavior as an intent to identify. A facial recognition process is triggered using the captured image data.

This image data is compared against biometric facial profiles stored either locally or in a remote cloud-based database. Upon a successful match, the system overlays a visible marker, such as an arrow or bounding box, around the matched individual within the user's field of view on the left lens 110. Concurrently, identification metadata is displayed on the right lens 111, which may include the individual's name, associated workplace, department, and last known interaction date 300.

For additional feedback, a directional speaker embedded in the eyewear frame may audibly relay the matched identification data. The speaker is positioned near the user's ear to deliver discrete audio without the need for external headphones, using technologies such as directional sound or bone conduction.

This embodiment of system 100 integrates facial recognition, gaze tracking, and AR overlay to enable users to identify and engage with known individuals in real time. The process is entirely hands-free and intuitive, requiring only natural gaze behavior to initiate identification—ideal for environments like stadiums, airports, or social gatherings.

Referring to FIG. 3, in one embodiment as an example use case, in crowded environments such as a stadium, airport, or tourist site, the system may employ the outward-facing cameras to capture a wide field of view encompassing multiple individuals. A facial recognition module may process the image data to identify persons stored in the user's contact database. The matched individual's identity, including name, affiliation, and last known interaction metadata 300, may be projected onto the lens 111 to facilitate social engagement. The system may also provide audible output of the identification data using the speaker positioned near the user's ear. The processing routine may be initiated by gaze fixation or a predetermined eye gesture to reduce manual input and enable hands-free operation.

Figure 4:
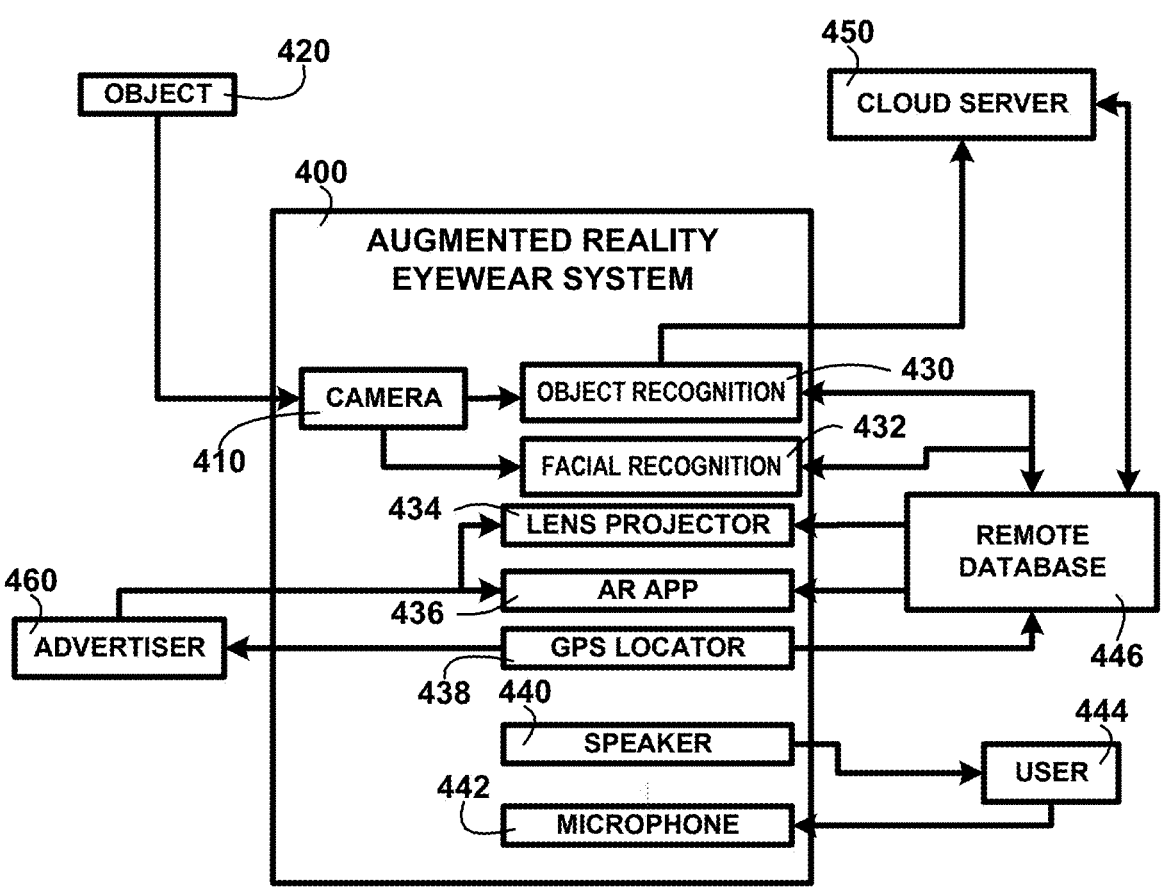
FIG. 4 shows a block diagram of an overview flow chart displaying images and data with augmented reality of one embodiment.

FIG. 4 illustrates a block diagram of an augmented reality eyewear system 400 configured to capture, analyze, and display contextual information about objects and individuals in the user's field of view. The system includes at least one outward facing camera 410 positioned on the eyewear frame to capture image data of an external object 420. This image data is processed by an object recognition module 430 which identifies the object based on visual features and matches it against stored entries in a reference database. Once the object is recognized, the relevant metadata is retrieved and presented to the user 444 through a projection module 434 embedded within the eyewear lens. The projection presents the information as a visual overlay aligned with the user's gaze. In parallel, the same information may be delivered audibly to the user via a speaker 440 integrated into the eyewear frame.

When the user 444 surveys a scene that includes a group of individuals, the system automatically activates a facial recognition engine 432 that begins scanning detected faces. These are compared against facial profiles stored in a remote database 446 containing biometric records of previously encountered contacts. The AR application 436 superimposes a live camera image of the group on the left lens for context. If the user directs gaze at a specific face within the group and performs an eye gesture—such as prolonged fixation or a blink sequence—the system initiates a targeted facial recognition process for that individual. Upon a successful match, the AR application 436 projects the person's identification data onto the right lens. This may include their name, workplace, department, and prior interaction history. The same information can be vocalized to the user via the embedded speaker 440 to enable discreet and hands-free interaction. This functionality allows the user to recognize and engage known individuals in real time based on visual input and biometric confirmation.

The system further includes a GPS module 438 that identifies the user's geographic location and correlates it with nearby landmarks or commercial entities. If the user fixates on a local business, such as a storefront or restaurant, and optionally issues a voice query through microphone 442, the system retrieves promotional or informational content from a remote cloud-based database 446 hosted on a server 450.

A location module coupled to the artificial intelligence application and GPS module 438 determines the location of a site or object vocalized by the user and queries the AI app to display via AR driving directions to assist the user in reaching the destination.

Advertiser specific content 460, such as operating hours or special offers, may then be projected into the user's visual field and optionally vocalized. This integrated use of gaze tracking, object and facial recognition, GPS localization, and augmented feedback enables a seamless and personalized augmented reality experience that adapts to user intent in real time.

As shown in FIG. 4, the system supports object recognition 430 and facial recognition 432 routines executed by a processor using image data from at least one outward-facing camera 410. In one embodiment as an example use case, during activities such as travel, sightseeing, or attendance at a sporting event, the user 444 may direct their gaze at an object 420 or individual within their field of view. The processor may initiate a recognition query to a remote database 446 via a wireless connection to a cloud server 450. Once identified, contextual data about the object or individual is projected onto the lens using a lens projector 434. For example, a user gazing at a historical monument may be presented with metadata including name, elevation, construction date, or notable facts, while facial recognition of a known contact may retrieve metadata from prior interactions. Information may also be concurrently delivered via an embedded speaker 440 for auditory reinforcement.

Figure 5:
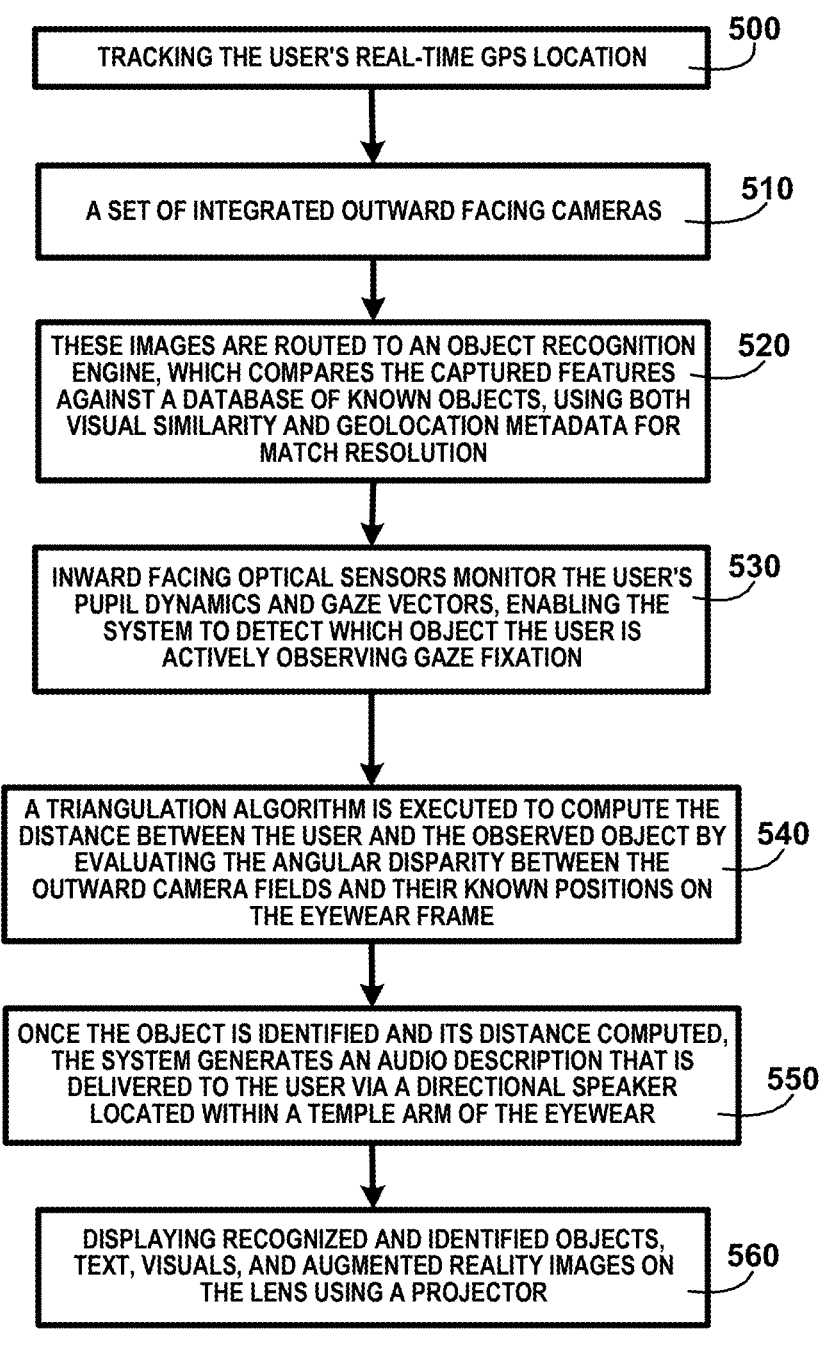
FIG. 5 shows a block diagram of an overview of one or more smart eyewear glasses automated modules of one embodiment.

FIG. 5 presents a block diagram illustrating the core functional modules of an automated augmented reality eyewear system, designed to process real time environmental, biometric, and geospatial inputs to generate dynamic visual and audio feedback. The system includes a GPS tracking module 500 configured to continuously determine the user's geographic location, enabling contextual relevance for subsequent recognition and display functions.

A set of integrated outward facing cameras 510 captures real time images of the user's field of view. These images are routed to an object recognition engine, which compares the captured features against a database of known objects, using both visual similarity and geolocation metadata for match resolution 520. The combination of image content and GPS location enhances the system's ability to correctly identify context specific landmarks, items, or commercial targets.

In parallel, inward facing optical sensors monitor the user's pupil dynamics and gaze vectors, enabling the system to detect which object the user is actively observing gaze fixation 530. A triangulation algorithm is executed to compute the distance between the user and the observed object by evaluating the angular disparity between the outward camera fields and their known positions on the eyewear frame 540.

Once the object is identified and its distance computed, the system generates an audio description that is delivered to the user via a directional speaker located within a temple arm of the eyewear 550. The user simultaneously receives visual confirmation in the form of an augmented overlay displayed on the lens surface by a miniature projection system 560. The overlay may include the object name, measured distance, associated metadata, or commercial offers relevant to the object. The combination of visual and auditory outputs, triggered by gaze tracking and enhanced by GPS and computer vision, provides the user with a seamless, automated interface for exploring and interacting with their surroundings.

FIG. 5 further illustrates system modules that track the user's real-time GPS location 500, capture image data 510, and calculate distances to objects based on image-derived triangulation 540. In one embodiment as an example use case, during activities such as urban walking, bicycling, or hiking, the GPS module and object recognition system may jointly identify waypoints or hazards (e.g., approaching intersections, trailheads, or vehicular traffic), and visually or audibly alert the user through lens projections 560 and speaker messages 550. The combination of real-time positioning, automated recognition, and projection enables the system to function as a context-aware wearable interface for environmental navigation and safety augmentation during both recreational and utilitarian movement.

Figure 6:
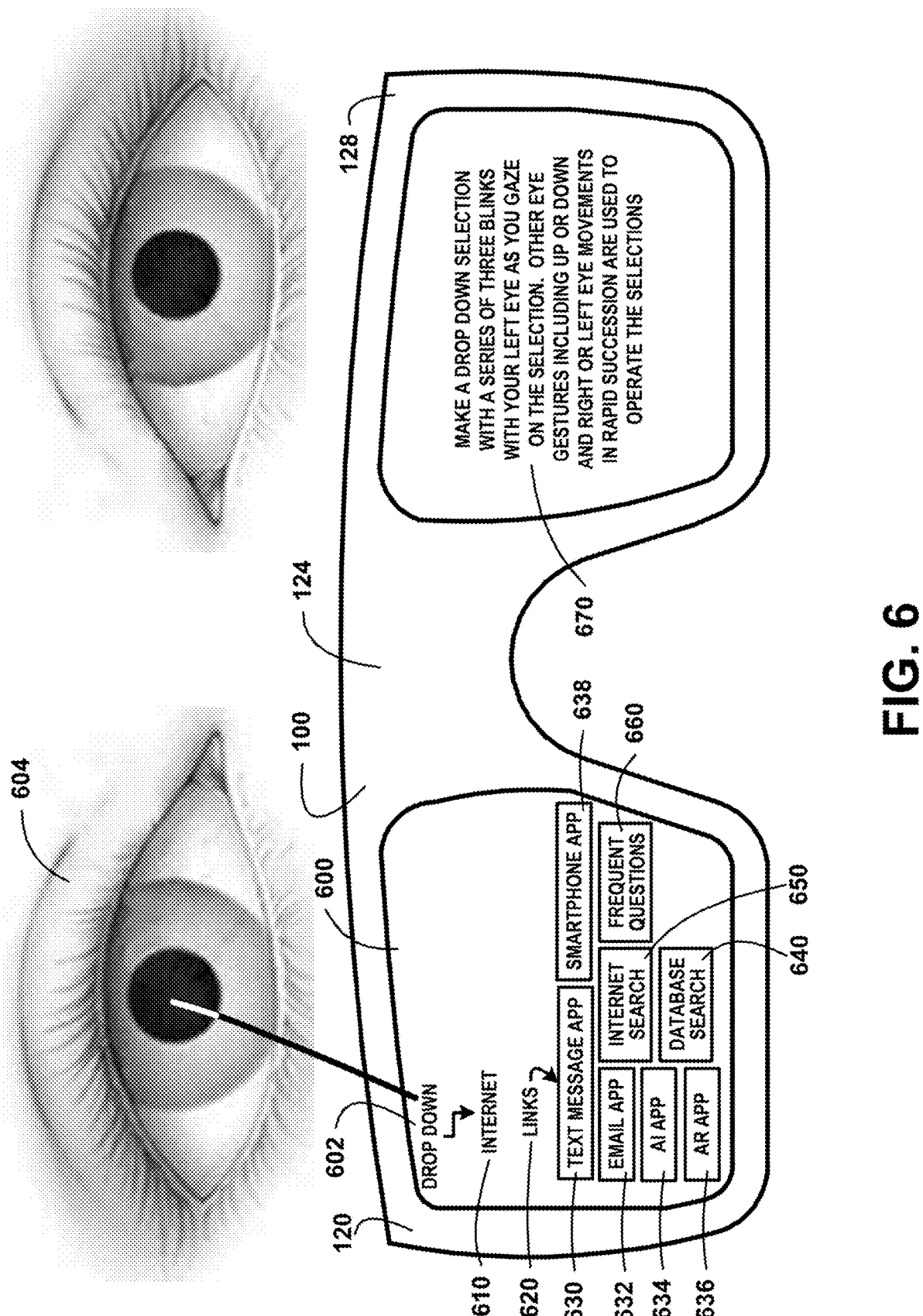
FIG. 6 shows for illustrative purposes only an example of a user visually activating one or more smart eyewear glasses automated modules of one embodiment.

FIG. 6 illustrates an embodiment of user interaction with the augmented reality eyewear system 100 through gaze directed activation of visual interface modules. The eyewear includes outward facing cameras 120, 124, and 128 that collectively provide a composite field of view 122, 126, and 130 of FIG. 1. These fields are aligned with the user's natural binocular vision and are directed toward external environmental content. The user is shown engaging the right lens 600 by directing visual attention toward a predefined activation region 602 mapped within a virtual coordinate grid embedded in the lens surface. Each lens is digitally segmented into addressable coordinate zones, which are associated with interface elements or system commands.

Inward facing infrared cameras monitor the user's pupil position and movement in real time. When gaze fixation aligns with a stored coordinate corresponding to a system control region, such as the drop-down activation zone 602, the onboard processor resolves the grid coordinate being observed. The system then interprets this gaze event as an intent signal, enabling the user to activate menu modules solely through eye movement without the need for touch or voice commands.

A series of predefined eye gestures may be used to select, navigate, or confirm commands within the displayed menu interface. Recognized gestures include voluntary blinks, prolonged eye closure, or directed glances in up, down, left, or right vectors at predetermined speeds and intervals. In the illustrated embodiment, the user activates a concealed drop-down interface by performing a gaze fixation followed by a triple blink sequence with the right eye 604. Upon detection of this gesture, the system projects a main control menu onto the lens surface, including modules such as an internet portal 610 and link selector 620.

When the user selects the links module 620, the system expands the interface to display additional application shortcuts 630, including a smart phone app 638 having a text messaging app 630, email interface 632, artificial intelligence assistant 634, augmented reality content loader 636, database query tool 640, internet search module 650, and a frequently asked questions knowledge base 660. Each selection can be made using gaze fixation paired with gesture input, such as a blink or rapid eye movement. Gesture logic 670 interprets these inputs to execute the desired selection. This configuration enables the user to fully navigate system functionality using only natural eye movements, maintaining hands free control of the augmented reality experience. The smart phone app having a text messaging app, email interface allows the user to check emails, send text messages and place a smartphone call.

Figure 7:
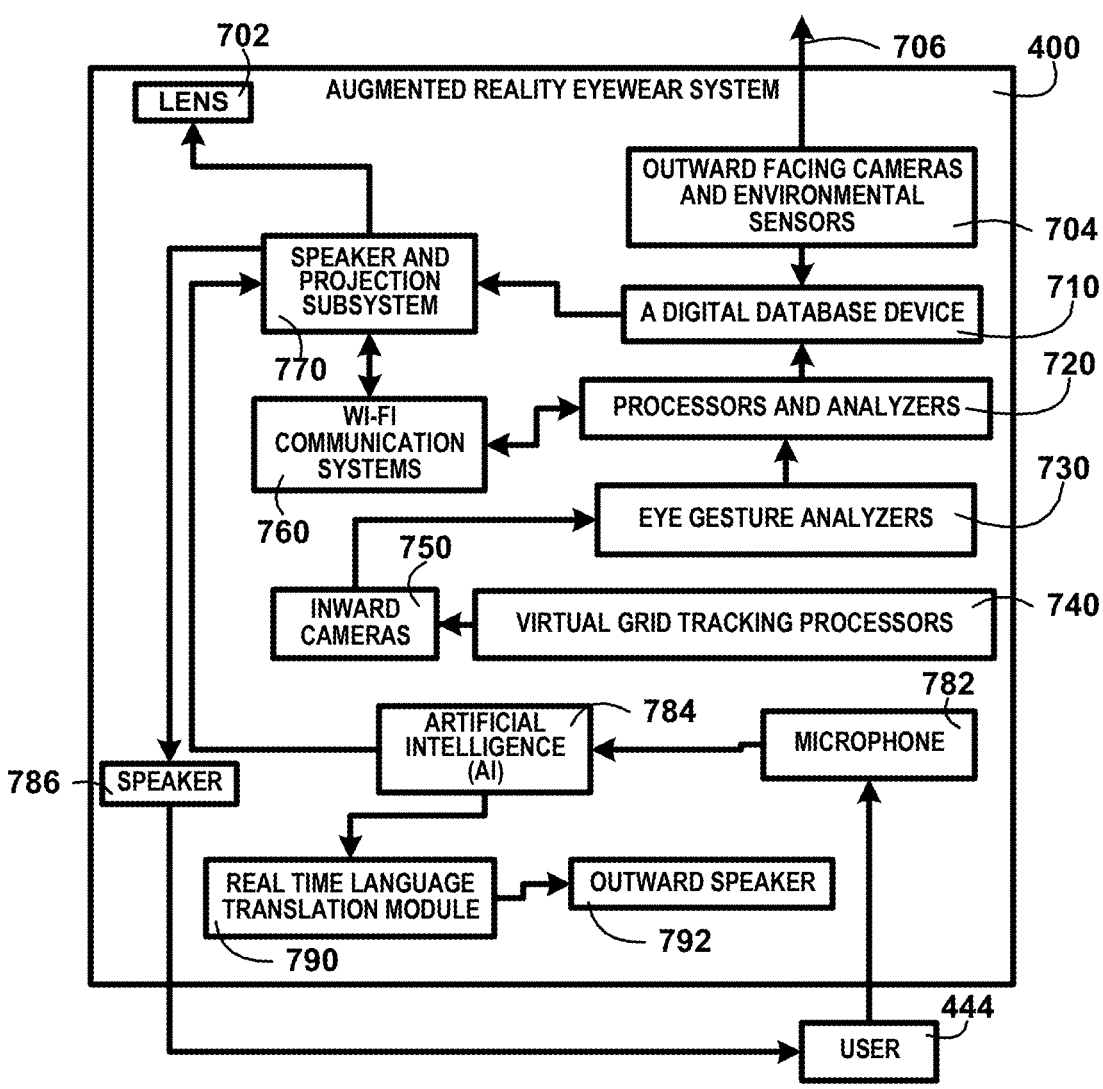
FIG. 7 shows a block diagram of an overview of smart eyewear devices of one embodiment.

FIG. 7 presents a block diagram illustrating key components of the augmented reality eyewear system 400 in one embodiment. The system includes left and right optical lenses 702, which serve as transparent display surfaces for augmented content. A network of outward facing cameras and environmental sensors 704 is mounted along the frame and lens periphery to provide a wide composite field of view 706 for external scene analysis. The system is further equipped with a digital database device 710 configured to store both environmental imagery and user-specific biometric data. Image analysis and control logic are handled by a set of processors and analyzers 720 that perform real time computational tasks.

Eye gesture analyzers 730 interpret ocular movements as input commands, based on detected variations in gaze direction and blink patterns. Virtual grid tracking processors 740 map pupil position to discrete locations on the lens, enabling context-specific responses. Inward facing cameras 750 monitor the user's eye position, pupil dilation, and fixation duration with high temporal resolution. Communication with remote servers and cloud-based services is enabled via a Wi-Fi communication module 760. A speaker and projection subsystem 770 delivers audio feedback and lens-based image projections in response to user interaction. In one scenario, the user 444 may initiate a spoken query into a microphone 782, invoking an artificial intelligence application 784 hosted locally or remotely. The system then returns a contextual response, delivered to the user through an embedded speaker 786. The artificial intelligence application 784 includes a real time language translation module 790 to interpret textual signs and displays the translation via an AR projection onto the transparent display surfaces and broadcasts an audible translation from a person over the speaker. The real time language translation module includes a translation of the user's verbal response with a translation broadcasted using an outward speaker 792 embedded on the front of the frame for interactions with others.

Also, in one embodiment, pupil dilation and gaze fixation data, once analyzed, can serve as implicit indicators of heightened user interest. Upon detecting such responses, typically characterized by a dilation threshold sustained over a minimum duration while fixated on a particular grid coordinate, the system's processor triggers content delivery protocols. In response, the augmented reality (AR) projection system embedded in one or both lenses can selectively present relevant digital content aligned with the object of interest. This may include superimposed text, contextual data overlays, multimedia, or interactive menus. For instance, if a user exhibits dilated pupils while viewing a historical monument, the system may display its name, construction date, and relevant cultural facts. In commercial contexts, gaze-driven dilation on a storefront may activate AR coupons, directions, or product showcases. The system may also initiate an audible description or AI-driven interaction through embedded speakers, enabling a seamless and hands-free flow of information tailored to the user's inferred cognitive and emotional state.

The outward facing cameras and sensors 704 operate in continuous or periodic capture mode, acquiring visual and contextual data from both the user's environment and the user's own biometric profile. Captured image sequences and sensor data—including pupil size, gaze vector, and retinal surface imaging—are stored within the local digital database 710. The processing unit 720 evaluates the incoming data stream to detect events of interest, such as changes in user engagement or fixation on specific objects. The eye gesture analyzer 730 decodes these patterns into commands that drive system behavior, particularly in response to gaze interaction with virtual grid regions projected on the lens surfaces.

The wireless communication module 760 allows the eyewear system to interact with cloud-based services, including email platforms, messaging systems, and content providers. Additionally, processor subsystems may assess the user's implicit attention levels toward physical or digital content—such as advertising, media, or individuals—based on biometric indicators. These metrics can be used in real time to adapt system outputs or may be logged for analytics purposes.

In this embodiment, the eyewear system also incorporates a sound and projection module that enables synchronized audio and visual messaging. Directional speakers deliver discrete audible content, while embedded projectors display images or text aligned with the user's visual perspective. Some configurations may include haptic or vibration feedback mechanisms to reinforce alerts or interactive prompts. The integration of virtual grid tracking processors with inward facing cameras 750 allows the system to detect and respond to precise eye movements and gestures mapped to digitally defined lens coordinates, enabling a natural, non-verbal control interface for navigating augmented content.

In another embodiment referencing FIG. 5 and FIG. 7, as an example use case, the wearable system may be configured to operate as a context-aware navigation assistant during dynamic pedestrian or cycling activity. The outward-facing cameras 704 capture environmental features in real-time while the GPS locator 500 of FIG. 5 tracks the user's precise location and heading. The processor 720 queries a local or remote database of mapped environments and overlays directional markers, alert zones, or highlighted destinations directly onto the user's visual field using lens projection modules 770. For example, during navigation through a city street, the system may identify points of interest, upcoming turns, or cautionary zones (e.g., high-traffic intersections) and display those data points within the AR view. The user may confirm a direction or route using an eye gesture interpreted by the gesture analyzers 730, eliminating the need for spoken input or physical device manipulation.

FIG. 8 illustrates a block diagram of an overview flow chart representing the functional modules and data flow within the augmented reality eyewear system in one embodiment. The system begins with continuous or periodic acquisition of visual and biometric data using integrated cameras and sensors 800 embedded within the eyewear frame and lens surfaces. These sensors are configured to monitor the user's eye field of vision, capturing high-resolution imagery of ocular features including pupil size, retinal position, and gaze direction.

Captured data is routed to a local or remote digital database device 810, where it is recorded and indexed for real time access and historical analysis. The system leverages digital processing modules 820 to perform advanced analytics on the incoming image and sensor data, including identifying trends in pupil dilation, tracking eye movement trajectories, and detecting gaze fixation duration.

Measurement and analysis systems 830 are embedded directly into the eyewear hardware and optically aligned with the user's eyes to ensure accurate biometric sampling. These systems include infrared illumination, optical filters, and digital signal processors configured to interpret reflected signals and generate actionable biometric profiles. The aggregated data from these embedded modules is further analyzed to extract meaningful patterns 840, such as cognitive load, attentional focus, or biometric indicators of user state. This architecture supports a closed-loop feedback system that allows the eyewear to adapt its augmented reality output based on the user's physiological inputs.

Figure 9:
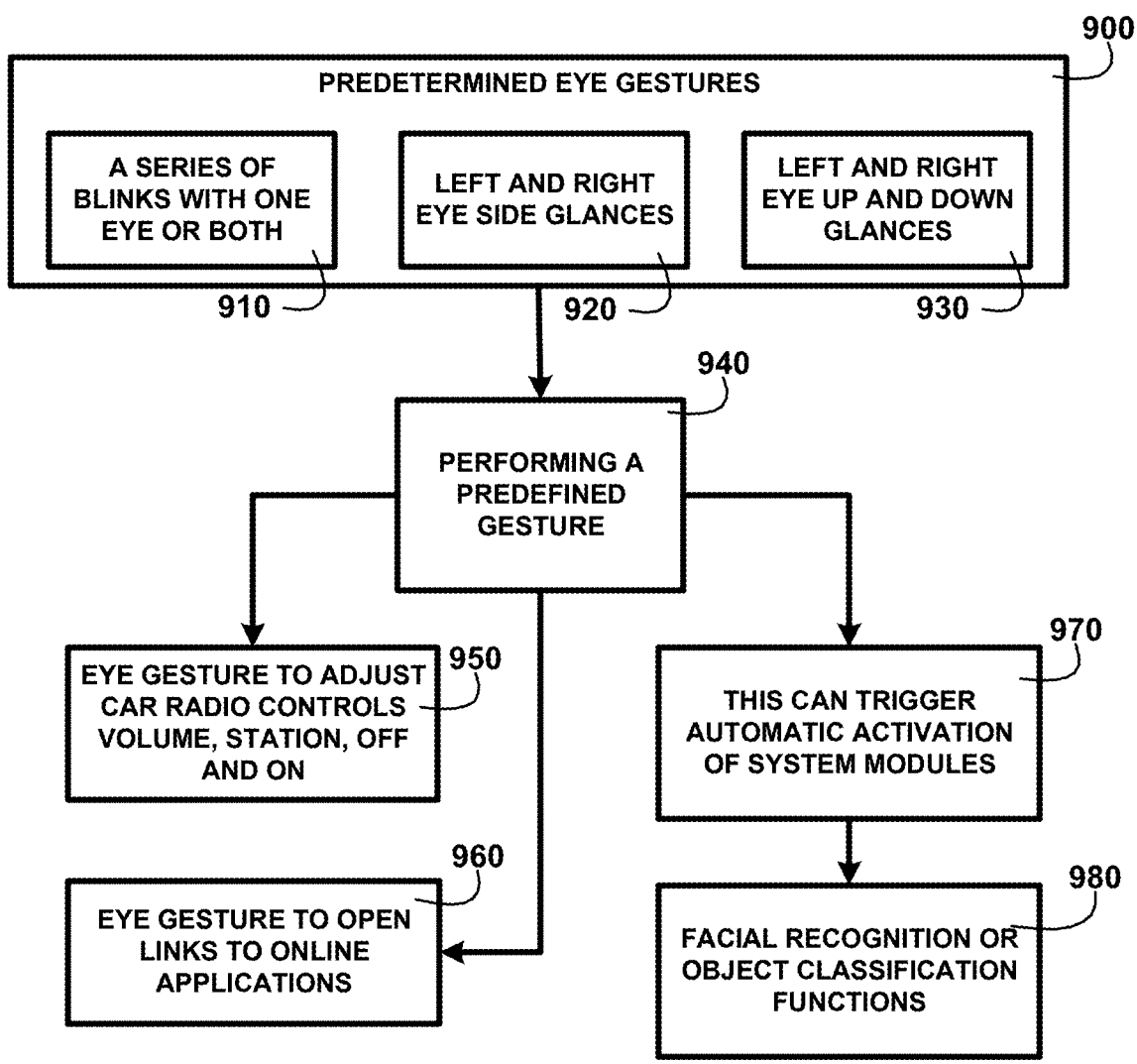
FIG. 9 shows a block diagram of an overview of predetermined eye gestures of one embodiment.

FIG. 9 presents a block diagram illustrating an overview of predetermined eye gestures 900 configured to control application selection and system operations within the augmented reality eyewear platform. These gestures are detected by inward-facing optical sensors that track real time changes in eye position, blink frequency, and gaze dynamics. Recognized gestures include a series of intentional blinks using one or both eyes 910, horizontal glances to the left or right 920, and vertical glances up or down 930. Each gesture is mapped to a discrete system function or interface control.

The user 444, as shown in FIG. 4, employs these eye gestures to interact with digital content in the visual field. For example, performing a predefined gesture 940 enables selection of digital objects or application icons presented on the lens, which in turn may activate features such as object recognition for a real-world item currently in view. In one embodiment, gesture-based controls may be extended to external devices. For instance, a specific eye movement sequence 950 may adjust settings on a nearby vehicle infotainment system, including volume control, station selection, or power toggling, without requiring manual contact.

Another application of gesture control involves the initiation of cloud-based or AI-driven services. An eye gesture sequence 960 mapped to a virtual grid coordinate on the lens may open a link to an artificial intelligence assistant, allowing the user to pose context-sensitive questions based on observed content in the environment. The system's processors continuously monitor gesture patterns and, upon detecting consistent gaze or repeated interactions with a particular object or individual, may interpret such behavior as a high-confidence indicator of user interest. This can trigger automatic activation of system modules 970, including recognition services or contextual data retrieval.

The augmented reality eyewear system incorporates an artificial intelligence (AI) module configured to process user-initiated queries and contextual scene data captured by outward-facing cameras. Upon detection of user gaze fixation or verbal input, the AI module—either embedded locally or hosted on a remote server—executes recognition algorithms using real-time image data, geolocation inputs, and user-specific preferences. The AI module retrieves contextual metadata from a database, including object or person identification, environmental descriptions, commercial offerings, or navigation information, and coordinates with a graphics processing unit to render the corresponding augmented overlay on the lens surface. In one embodiment, a user may initiate a spoken inquiry, such as "AI chat, how far to the next EV recharging station?", which is processed by the AI application using speech recognition and location data to generate a response projected visually and/or delivered audibly via a frame-integrated speaker. This AI-driven interaction enables hands-free, gaze-aware augmentation of the physical world through synchronized visual and audio feedback, providing a seamless and intelligent user experience.

Facial recognition or object classification functions 980 may also be launched via gesture-based commands. For example, a blink or glance sequence focused on a specific individual or structure may initiate a database query to identify the subject and present associated metadata within the user's augmented display. This gesture-based control architecture enables a fully hands-free and intuitive method for interacting with the augmented environment, driven entirely by natural ocular behavior.

As further shown in FIG. 6 and FIG. 9, the smart eyewear system may incorporate a virtual coordinate grid superimposed onto each lens 600, allowing inward-facing cameras 750 of FIG. 7 and processors 720 of FIG. 7 to detect gaze location and interpret predetermined eye gestures (e.g., triple blink, horizontal glance, vertical glance) as discrete control signals. This capability permits hands-free activation of applications and contextual routines during continuous use. In one embodiment as an example use case, a user may activate a translation module while walking in a foreign urban environment, by fixating on an AR-displayed menu or street sign and performing a designated eye gesture. The translation module, executed locally or on a connected remote platform, may extract text data via optical character recognition and overlay the corresponding translated content onto the lens. The user may also receive an audible playback of the translated phrase via the speaker 786 of FIG. 7. The eye-tracking and gesture-based input system enables seamless AR engagement without hand motion, ideal for wearable platforms that must minimize distraction and physical interaction.

As shown in FIG. 9, the system may further include hand gesture recognition functionality using the outward-facing cameras 120, 124, and 128 of FIG. 1 configured for high-frame-rate capture and motion tracking. The digital processor may perform spatiotemporal analysis of frames in the field of view to detect user-performed gestures, such as pointing, swiping, pinching, or air-tapping motions. Each gesture may be mapped to a corresponding software operation, such as opening an application, selecting a virtual item, or manipulating an AR-rendered object. Gesture recognition may be performed using model-based or machine-learning-based recognition algorithms, optionally supported by cloud-based computation resources via the communication module 760 of FIG. 7. The gesture-based control system provides an alternative or complementary interface to eye gestures and voice input methods.

In another embodiment, the system may support synchronized interaction with a plurality of wearable devices using a unified communication protocol. These may include smartwatches, fitness rings, haptic feedback gloves, and other body-mounted electronics capable of exchanging real-time data with the eyewear system. Bi-directional communication may allow the eyewear to act as a central hub, receiving biometric, location, or motion data from external devices while also transmitting display commands or contextual data (e.g., notification alerts or haptic signals) back to the wearables. For example, when the eyewear detects a physiological anomaly such as hypotension or arrhythmia, it may trigger a haptic pulse in a connected ring to alert the user discretely. Similarly, biometric thresholds or gesture-based confirmations may be used to authorize secure transactions or initiate medical telemetry uploads to a connected healthcare platform.

Figure 10A:
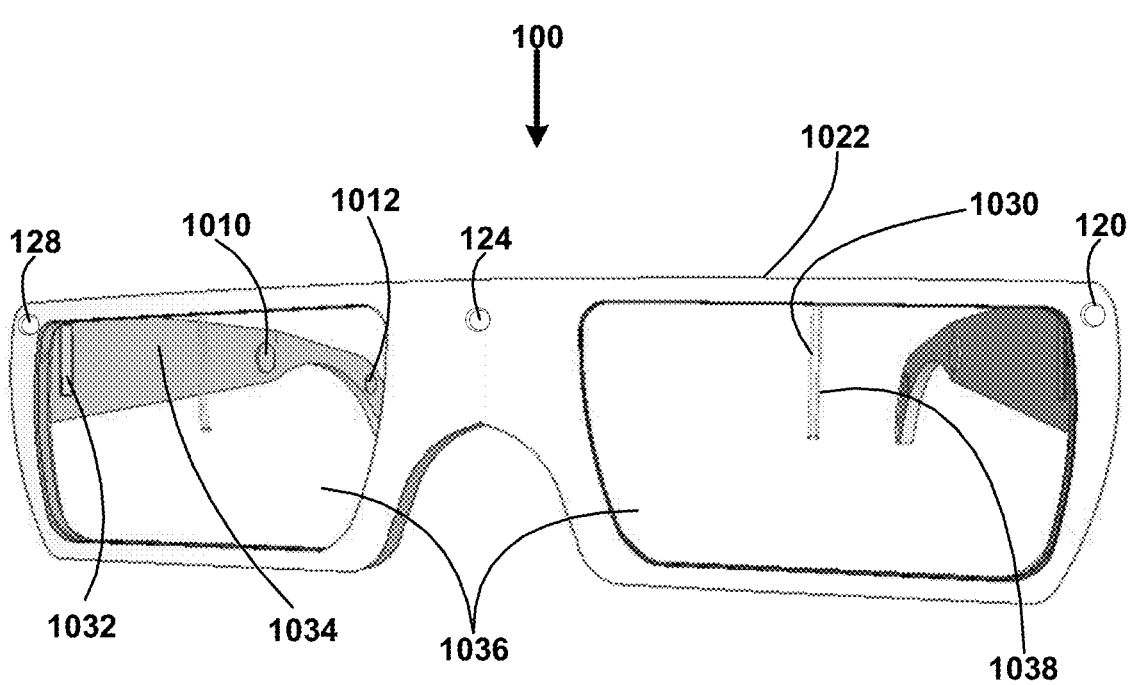
FIG. 10A shows for illustrative purposes only an example of a frame and lens fiber optic camera combination smart eyewear glasses of one embodiment.

FIG. 10A illustrates an embodiment of an augmented reality eyewear system incorporating a combination of frame-mounted and lens-embedded fiber optic camera modules. The augmented reality (AR) eyewear system 100 includes a structural frame 1022 supporting left and right lenses 1036. In this embodiment, at least two fiber optic camera modules 1038 are embedded directly into the transparent lens substrate. One of the embedded modules is configured with optical parameters suitable for imaging the external surface of the user's eye, including scleral boundaries and iris contours. The second embedded module is designed with a longer focal length and infrared sensitivity to focus through the pupil and capture high-resolution retinal imagery, forming a dedicated infrared retinal fiber optic camera 1030.

The eyewear frame 1022 also includes three outward facing environmental cameras 120, 124, and 128 strategically positioned to provide overlapping fields of view and enable stereoscopic imaging of external objects. These outward cameras support object and facial recognition, as well as spatial depth estimation through triangulation.

The frame is further configured with two temple sections 1034, each of which houses a set of sensory and feedback components. These include an audio alert speaker module 1010 positioned near the user's ear for delivering verbal or acoustic cues, and a vibration alert module 1012 mounted in contact with the bony area above the ear to transmit haptic signals through bone conduction. Each temple piece may also contain an alert light and projection unit 1032 capable of emitting light flashes or projecting textual notifications onto the internal lens surface. The integrated fiber optic cameras are visually indicated in the drawing using color coding for illustrative purposes only. In actual embodiments, these components are optically transparent and minimally intrusive to the user's field of vision.

Figure 10B:
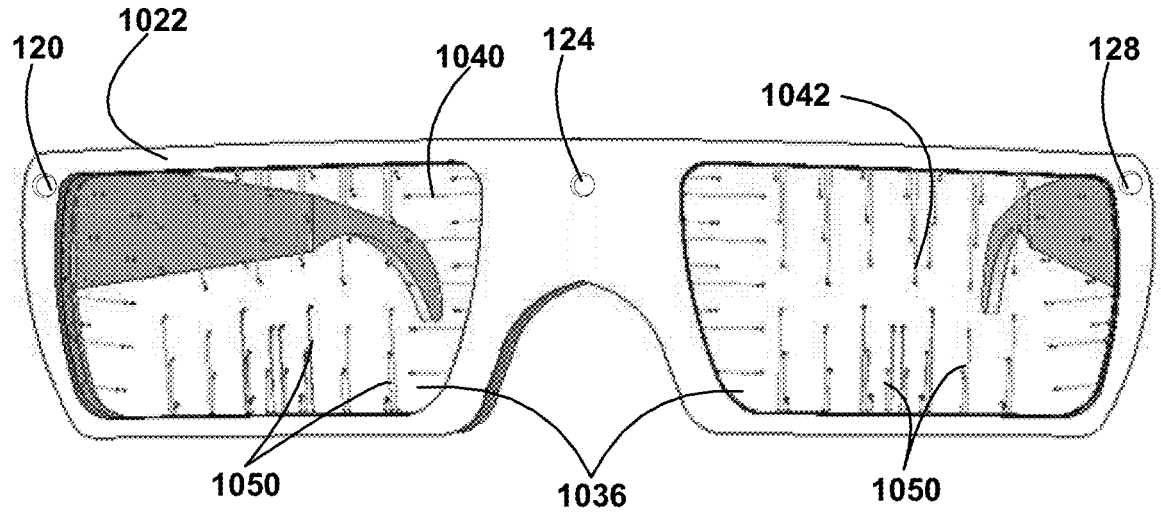
FIG. 10B shows for illustrative purposes only an example of a lens fiber optic camera smart eyewear glasses of one embodiment.

FIG. 10B illustrates an embodiment of an augmented reality eyewear system 100 incorporating a high-density array of lens-embedded fiber optic camera modules. The eyewear frame 1022 supports a pair of optical lenses 1036 and includes at least three outward facing environmental cameras 120, 124, and 128, arranged to provide wide field coverage and support depth perception, object recognition, and scene mapping.

In this embodiment, the eyewear lenses 1036 are embedded with a plurality of micro-scale fiber optic camera modules 1050, for example, as many as fifty-nine discrete units per lens. These modules are fabricated with varied optical focal lengths to serve complementary functions. A subset of the fiber optic cameras is configured to focus on the anterior surface of the eye, including the cornea, iris, and sclera, thereby enabling detailed monitoring of ocular positioning, blink rate, and torsional movement. At least one of the fiber optic modules is further configured to focus through the pupil and acquire high-resolution infrared images of the retina 1040, thereby functioning as an embedded retinal scanner 1042. This multilayered lens-integrated optical system supports continuous biometric monitoring without the need for bulky external sensors or obstructive hardware in the field of view.

Figures 11A, 11B:
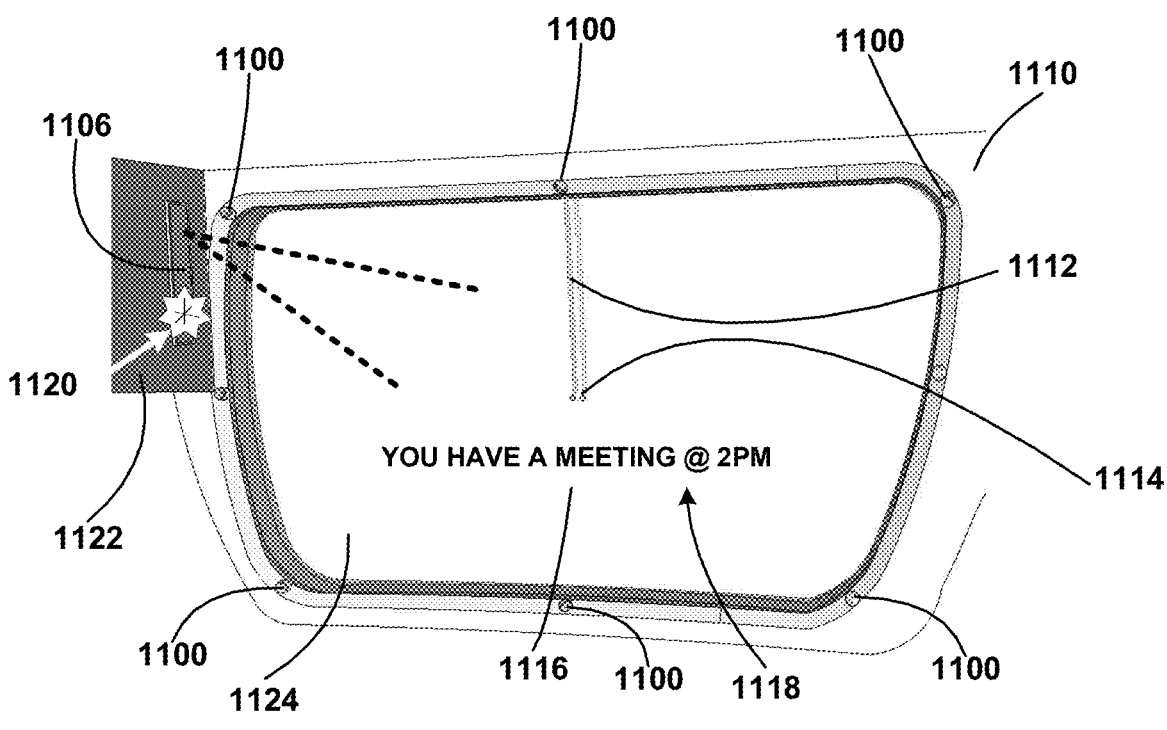
FIG. 11A shows for illustrative purposes only an example of frame fiber optic camera modules of one embodiment.
FIG. 11B shows for illustrative purposes only an example of frame-embedded image processor modules of one embodiment.

FIG. 11A illustrates an embodiment of the augmented reality eyewear system 100 incorporating frame-mounted fiber optic imaging modules and gesture tracking systems. The eyewear includes a structural frame 1022 of FIG. 10A and temple arms 1034 of FIG. 10A. Integrated into the eyewear lens 1124 are two optical imaging elements: a fiber optic camera 1114 designed for capturing high-resolution images of the external eye surface, and an infrared retinal fiber optic camera 1112 configured to image the retina through the pupil using infrared illumination. Mounted along the interior surface of the frame are a plurality of inward-facing eye gesture tracking cameras 1100. These cameras monitor gaze direction and pupil movements relative to a virtual coordinate grid to detect user intent and initiate application-specific functions.

The temple 1034 of FIG. 10A includes an alert and messaging projector module 1106 capable of displaying real-time notifications onto the lens surface, such as calendar-based reminders. For instance, a meeting alert stating "you have a meeting @ 2 pm" 1116 may be automatically generated based on data retrieved from the user's digital calendar 1118. The display timing may be dynamically adjusted in accordance with the user's real-time GPS location 500 as shown in FIG. 5, allowing for predictive notifications based on travel time.

A gyroscopic head tilt sensor module 1110 is embedded within the frame 1022 of FIG. 10A and is configured to track head orientation. A bright light flash 1120 alert signal embedded in the temple frame 1122. Data from this module is used to correct and calibrate the output of the eye gesture tracking cameras 1100, ensuring accurate gaze mapping even as the user changes head position. This helps maintain consistent control of virtual interface elements across different viewing angles and user motion conditions.

FIG. 11B shows an internal view of the eyewear frame 1022 of FIG. 10A illustrating the arrangement of embedded image processor modules used to analyze captured ocular data. Included within the frame is a forward-facing frame camera lens 1150 and an associated fiber optic transmission line 1160 that routes image data to a left eye image processor 1140. This processor receives raw visual input and performs preprocessing tasks that include spectral filtering and infrared imaging.

An image filter module 1180 applies selective wavelength filters to enhance visual contrast between anatomical features of the eye, such as the iris and pupil. An image infrared module 1170 is configured to detect thermal signatures or infrared reflectivity patterns that assist in imaging internal ocular structures under varying lighting conditions. A mirrored configuration is implemented for the right eye, using a separate image processor 1130, along with its own image filter module 1180 and infrared imaging module 1170. These right eye components are embedded within the eyewear's nose bridge, forming a balanced and compact imaging array.

The system architecture is designed to independently capture and process data from the left and right eyes. This dual-channel configuration enables separate pupillary and retinal assessments, which are critical for diagnostic precision. Ocular abnormalities may manifest asymmetrically across eyes due to factors such as localized neural deficits or asymmetric vascular supply. Independent analysis of each eye allows the system to detect unilateral conditions more effectively and helps isolate the affected physiological pathway, thereby streamlining clinical diagnosis and enabling faster and more accurate treatment planning.

Figure 12:
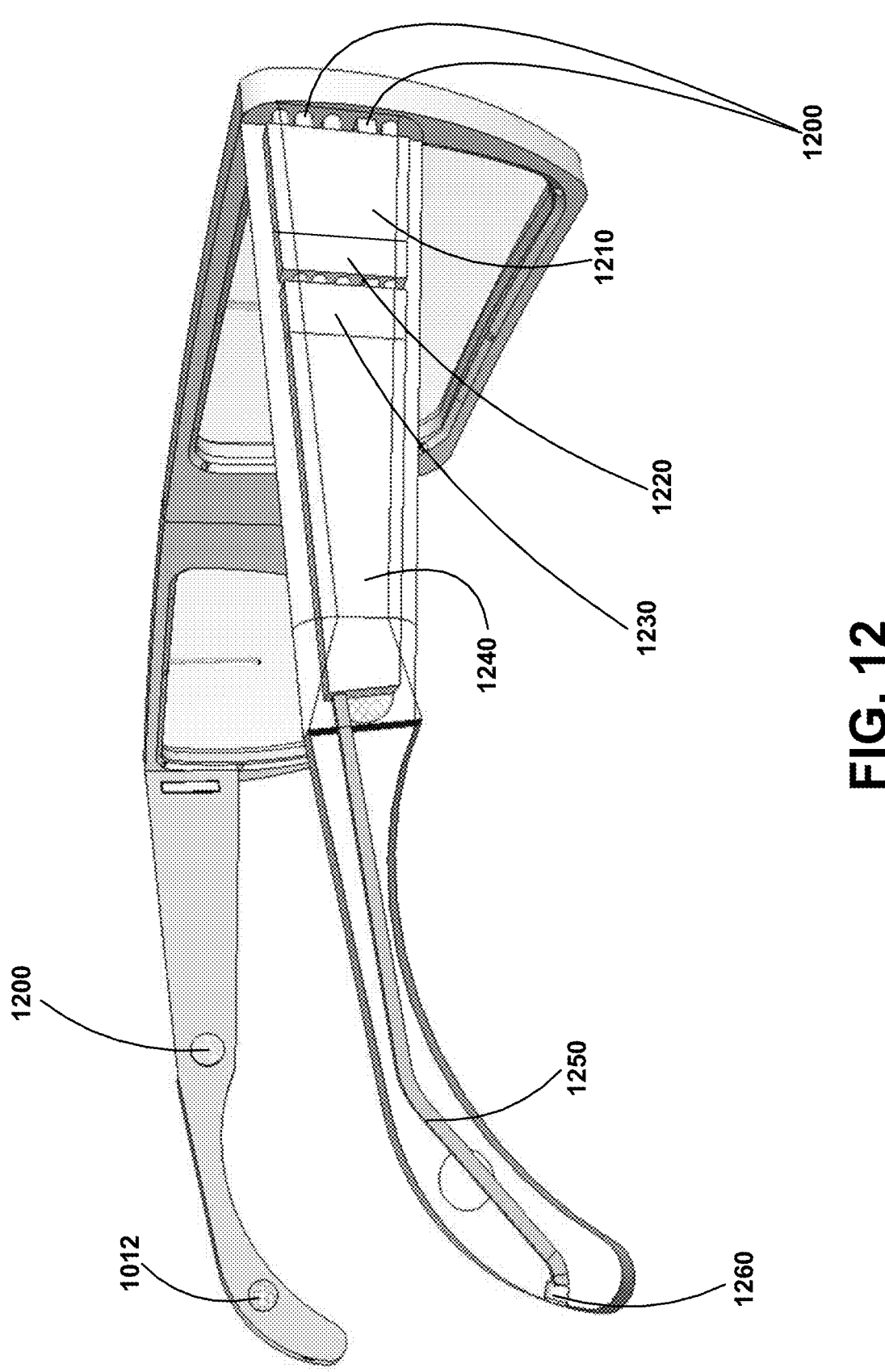
FIG. 12 shows for illustrative purposes only an example of temple-embedded component modules of one embodiment.

FIG. 12 illustrates an embodiment of the augmented reality eyewear system showing a detailed view of temple-embedded component modules. These modules are housed within the structural temple arms of the eyewear frame and are installed during the pre-molding phase of fabrication. The embedded architecture includes electrical and optical interconnects 1200 such as fiber optic lines, data transmission cables, and power conductors routed through the interior channel of the temple arms.

The module configuration includes a compact digital processor and an associated digital storage device, both positioned to support real time computation and local data logging. An alert generator module 1210 is included to coordinate system-level feedback, such as notifications, haptic alerts, or visual warnings. A wireless communication unit 1220 provides connectivity via Wi-Fi or other wireless standards, enabling synchronization with cloud-based services or paired devices.

Power is supplied by integrated rechargeable battery modules 1240, which receive input through a power distribution network including embedded data and power cables 1250. A USB connector module 1260 provides external access for charging, data transfer, or firmware updates.

In one embodiment, a photovoltaic energy harvesting module 1230 is integrated into the temple structure. This module converts ambient light—channeled through fiber optic cables—into electrical energy, which is used to supplement or recharge the battery system 1240. On the inner surface of the opposing temple, an audio alert speaker module 1010 of and a vibration alert module 1012, as previously shown in FIG. 10A, are embedded to provide haptic and auditory feedback to the user.

This compact and distributed component layout enables continuous system operation, user interaction, and sensor communication while preserving ergonomic balance and unobtrusive form factor.

Figure 13:
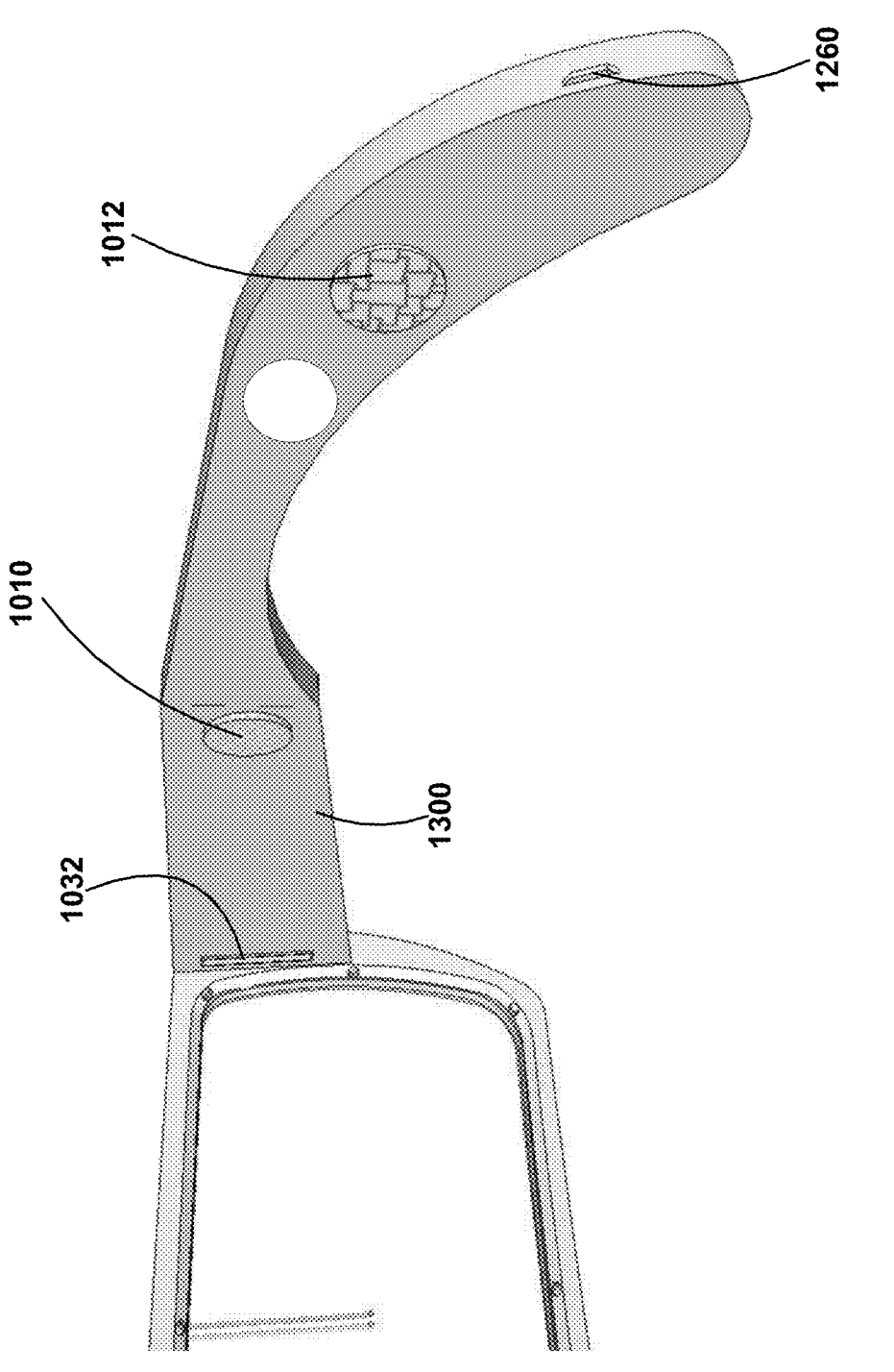
FIG. 13 shows for illustrative purposes only an example of driver alert modules of one embodiment.

FIG. 13 illustrates an embodiment of the augmented reality eyewear system incorporating driver alert modules designed to provide multi-modal warnings to a drowsy or distracted user. The depicted configuration includes an alert light and message projection module 1032, an audio alert speaker module 1010, and a vibration alert module 1012. These components are embedded within the temple arms and surrounding structural regions of the eyewear frame. A USB connector module 1260 is also shown, located near the non-hinged terminus of temple piece 1300, providing access for data transfer and power delivery.

The driver alert system is designed to initiate proactive sensory feedback in response to biometric indicators of drowsiness, inattention, or pupillary non-responsiveness. The audio alert speaker module 1010 is configured to emit non-rhythmic acoustic patterns and synthesized voice commands. Unlike standard notification tones, the audio signals vary dynamically in pitch, amplitude, and interval to avoid habituation and to promote auditory arousal. Example voice alerts include directives such as "wake up," "pull over," or "stop driving," which are played at escalating volume levels if the user's alertness fails to recover.

The alert light and message projector 1032 serves as a visual warning system by projecting context-specific messages directly onto the internal lens surfaces. These visual alerts may include flashing or animated text such as "wake up," "pull over," or "stop driving." The projected visuals are designed to be highly salient, using variations in font size, color contrast, blinking frequency, and brightness intensity—including full lens flashes—to forcibly recapture the user's visual attention.

Complementing the visual and auditory warnings, the vibration alert module 1012 delivers haptic feedback through the temple frame near the user's mastoid bone, as well as optionally through the nose bridge of the frame. These vibrations are non-periodic and randomized in frequency, amplitude, and waveform to prevent desensitization or entrainment to a steady rhythm. The combined effect of these multi-sensory alert channels is to counteract drowsiness in real time.

The USB connector module 1260 also supports additional functionalities. It enables data transfer of biometric records—such as pupillary images and sensor logs—from the eyewear's internal digital storage to a health monitoring system or patient record. It also serves as a direct charging port for the rechargeable battery modules 1240 described in FIG. 12. In an alternate embodiment, the eyewear may be placed on an inductive charging platform, where power is wirelessly transferred to the batteries without requiring physical connection.

Figure 14:
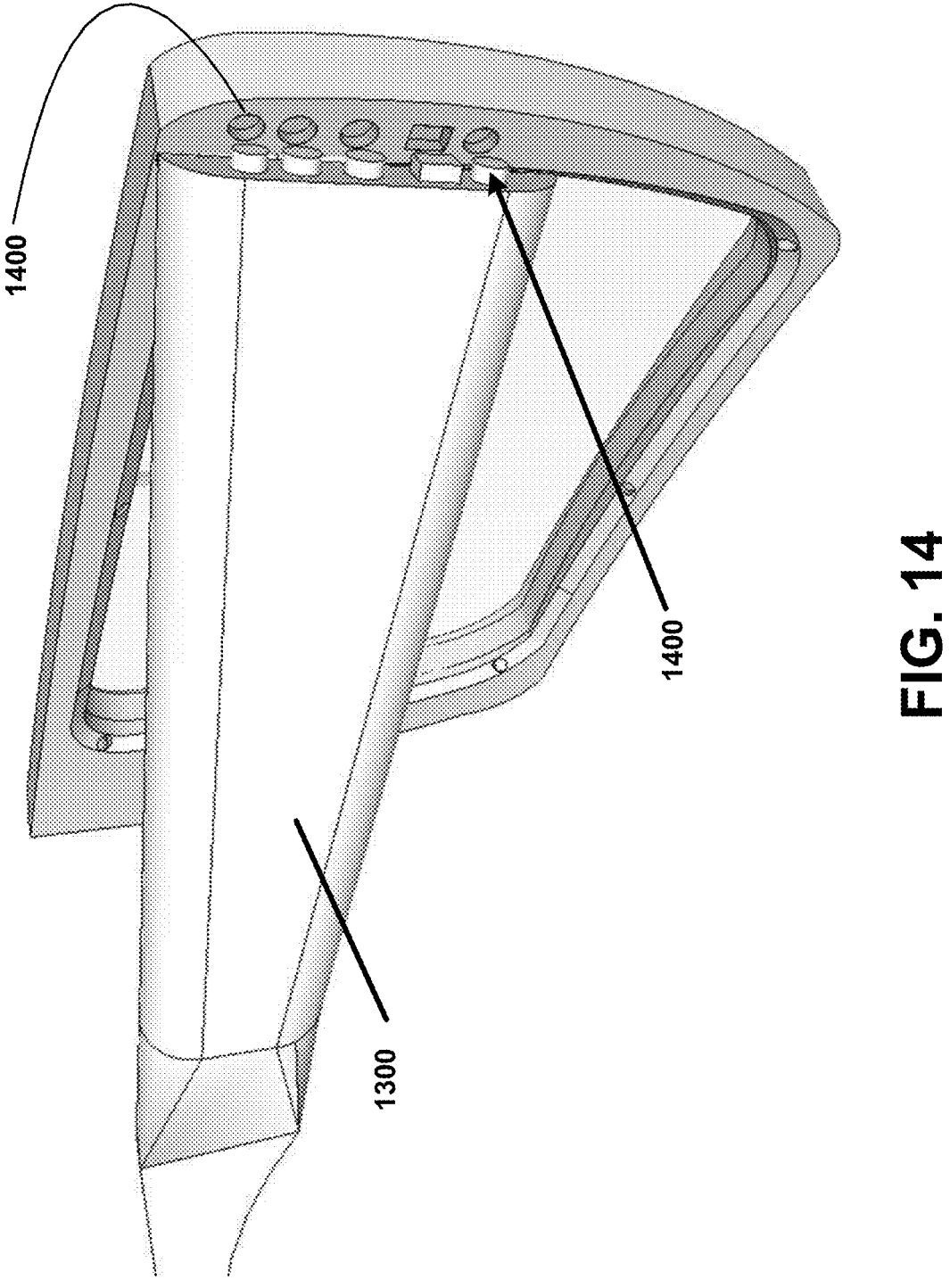
FIG. 14 shows for illustrative purposes only an example of hinged temple connections of one embodiment.

FIG. 14 illustrates an embodiment of a hinged connection mechanism for temple-mounted components within the augmented reality eyewear system. The temple piece 1300 is configured to support integrated electrical and optical transmission infrastructure, including power lines, fiber optic conduits, and digital data cables. These transmission lines extend from the hinged end of the temple arm and are designed to interface with recessed connection receptacles located in the main eyewear frame body.

When the temple piece 1300 of FIG. 13 is swung into the closed position, the extended connectors engage with their corresponding receptacles, thereby completing the electrical power connections, aligning fiber optic butt couplings, and enabling digital data transfer through circuit contact points 1400. The completed interface allows uninterrupted communication between temple-mounted modules and the core system components within the frame, including processors, memory, and projection systems. When the temple is opened or removed, the connectors disengage, resulting in disconnection of the power supply, interruption of data circuits, and decoupling of optical pathways. This configuration allows the eyewear to conserve energy by isolating active circuitry and preventing unnecessary battery drain when not in use. The modular design also facilitates maintenance and component upgrades by allowing quick disconnection and reattachment of the temple subsystem.

The system further incorporates biometric personalization and security functions based on ocular anatomy and pupil dynamics. The user's orbital muscles, including the ciliary muscles that regulate iris constriction and dilation, exhibit unique physiological characteristics across individuals. These include distinct iris patterns, orbital geometry, and pupillary reflex behaviors that are stable and quantifiable. The eyewear system can capture and analyze these biometric signatures using the lens-embedded and frame-mounted imaging modules described in previous figures.

In one application, the eyewear may be used as a secure identity authentication device. For example, when a user initiates an automated teller machine (ATM) transaction, instead of relying on the ATM's embedded camera—which may be obstructed by sunglasses or hats—the user's eyewear transmits previously registered eye movement patterns and iris images directly to the ATM system for identity verification. This remote biometric authentication may supplement or replace conventional authentication methods such as PIN entry or fingerprint scans.

Additionally, the eyewear system supports remote control of external devices via calibrated eye movement commands, enabled through integrated wireless communication modules. Specific gaze directions and eye gesture sequences may be mapped to device functions. For example, a stored image of a car's dashboard radio interface can be loaded into the eyewear system. When the system detects the user's gaze matches the reference image on the actual device, a predefined gesture—such as three rapid blinks—can trigger an associated control action. An upward glance may increase the volume, a downward glance may lower it, and lateral eye movements can switch stations or activate seek functions. This non-contact, gaze-based control scheme extends to other remote interfaces in smart homes, medical equipment, or industrial systems, enabling intuitive and hands-free device interaction.

Figure 15:
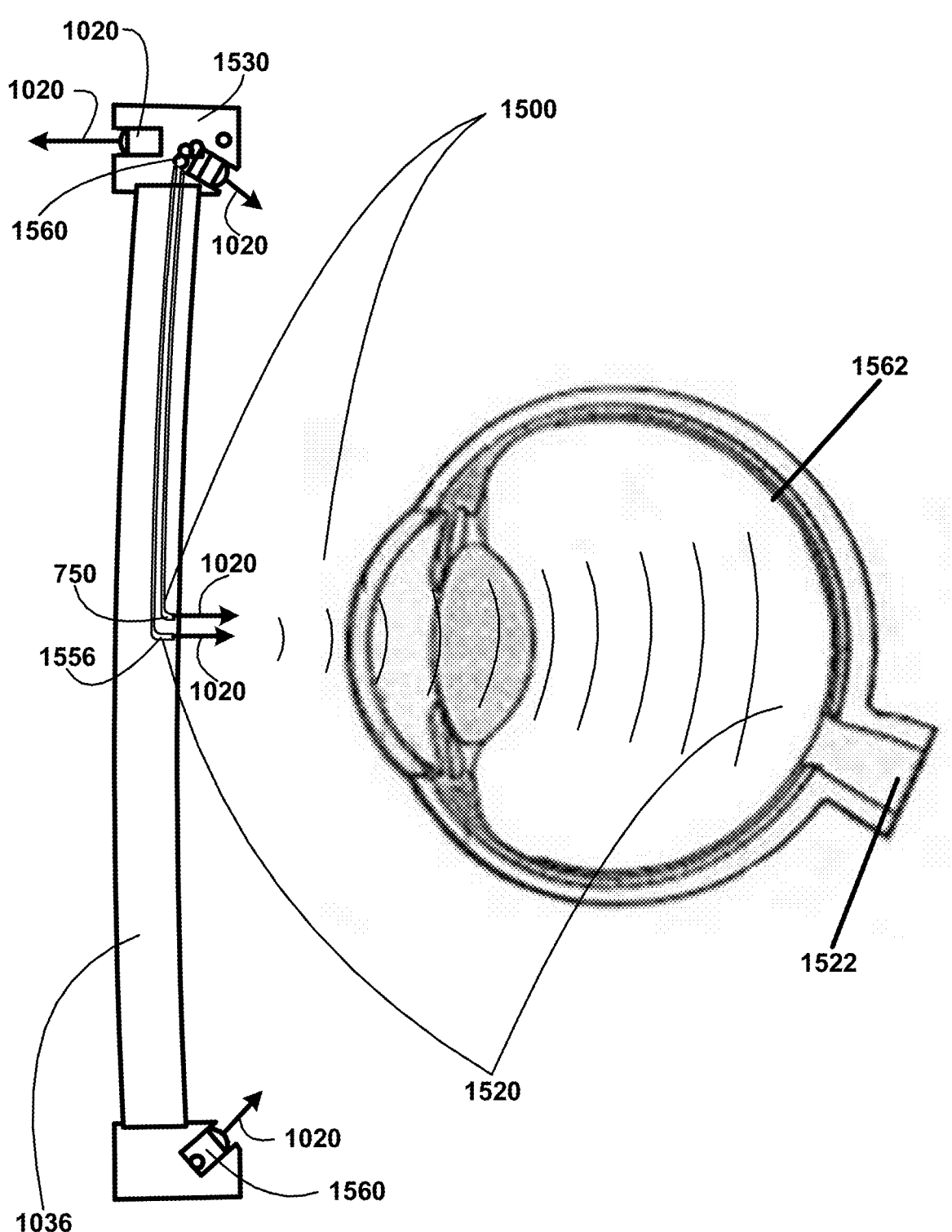
FIG. 15 shows for illustrative purposes only an example of eyewear camera focal lengths and field of views in a cross-section view of one embodiment.

FIG. 15 presents a cross-sectional view of an augmented reality eyewear system, illustrating the relative focal lengths and fields of view of various embedded camera modules. The eyewear includes a frame 1530 and an optical lens 1036 into which multiple imaging components are integrated. An infrared retinal fiber optic camera 750 is embedded within the lens and configured with an optical focal length and field of view 1520 designed to image internal ocular structures, including the retina 1562 and the optic nerve 1522. This module enables detailed biometric and medical imaging of the eye's interior using infrared illumination.

Also embedded in the lens is a second fiber optic camera 1556 with a focal length and field of view 1500 tuned to image the anterior surface of the eye, including the iris, sclera, and eyelid margins. Both imaging modules route their captured signals through fiber optic transmission lines 1160 of FIG. 11B embedded within the eyewear frame, enabling real-time processing by onboard or remote image processors. Other inward facing camera 1560 gathers pupillary tracking movements.

Additionally, the eyewear frame 1530 includes outward-facing environmental camera modules 1150 of FIG. 11B and 1020. These outward cameras are positioned to align with the user's forward line of sight and are configured to capture scenes within the user's field of view. The outward cameras operate continuously or in response to specific triggers, capturing contextual video or still images of the external environment. In certain embodiments, the outward camera 1020 is configured to function as a passive monitoring system, recording events such as vehicle motion or roadway activity. This feature allows the eyewear to act as a personal black box, preserving video evidence in the event of an accident or other real-world incident, regardless of whether the user is awake or unconscious at the time of the event.

Figure 16:
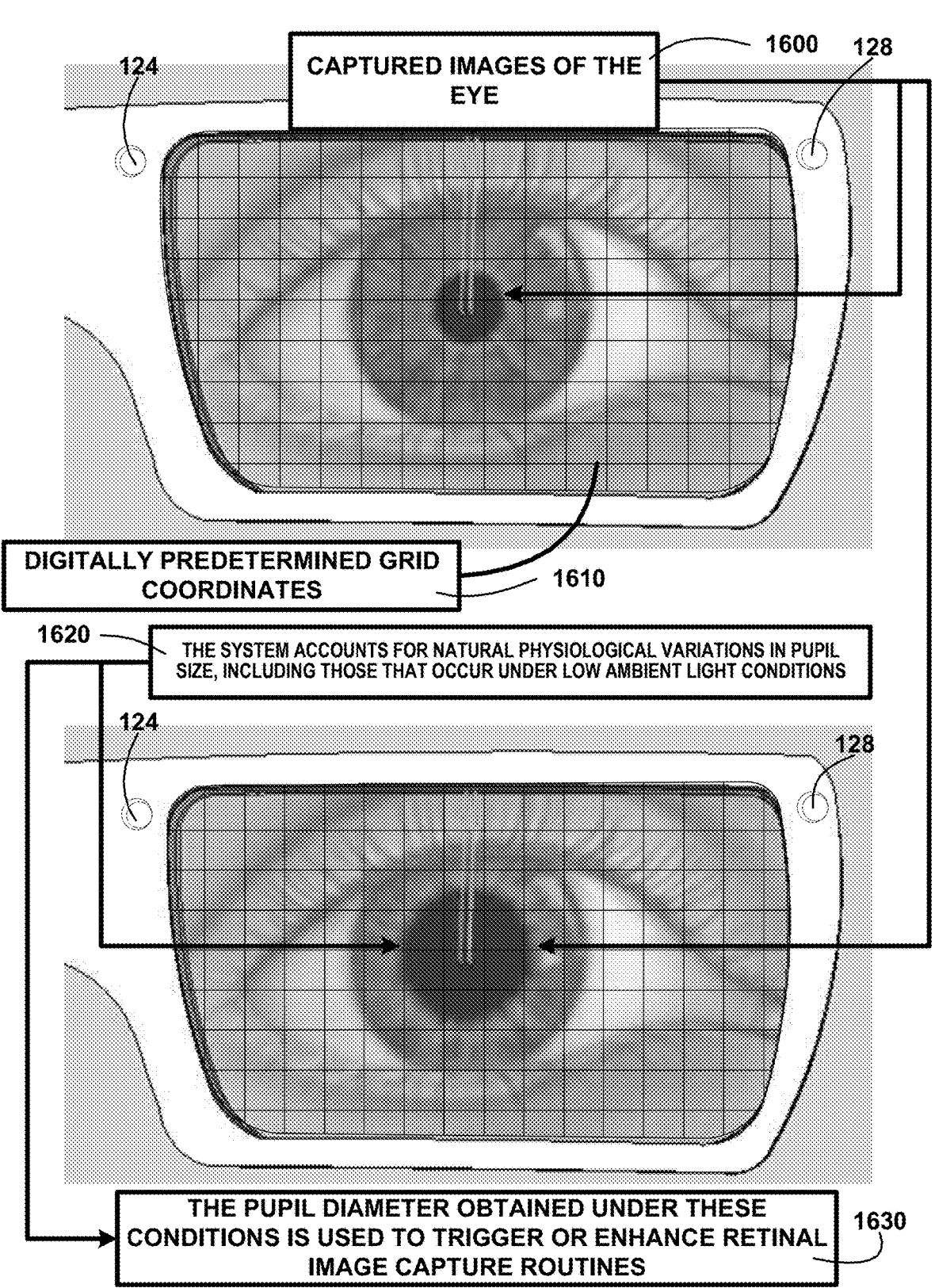
FIG. 16 shows for illustrative purposes only an example of pupil size measurements of one embodiment.

FIG. 16 illustrates an embodiment of the augmented reality eyewear system configured to measure and analyze pupil size using embedded optical sensors and digital image processing techniques. The system employs a set of digitally predetermined grid coordinates 1610 generated by onboard processors to spatially map the eye region and analyze pupil and retinal image data with high positional accuracy. These grid coordinates serve as a reference framework for interpreting incoming image signals and isolating the pupillary boundaries for measurement. The system includes three outward-facing cameras 120, 124, and 128 and FIG. 16 shows two of those cameras 124 and 128.

Captured images of the eye 1600, obtained using visible light or infrared (IR) imaging systems, are processed to detect contrast differentials between the iris and the pupil. This enables the system to determine the absolute pupil diameter and assess whether the pupil is in a dilated or constricted state. The system accounts for natural physiological variations in pupil size, including those that occur under low ambient light conditions 1620, which are common throughout the day due to environmental lighting changes.

When low light conditions are detected, the system automatically shifts to infrared-based imaging to enhance contrast and maintain measurement accuracy. The pupil diameter obtained under these conditions is used to trigger or enhance retinal image capture routines 1630, allowing the system to perform detailed biometric assessments using infrared retinal imaging. This functionality supports both medical diagnostics and user attention monitoring in variable lighting environments.

FIG. 7 and FIG. 8 illustrate embodiments supporting real-time physiological monitoring. The inward-facing IR cameras 750 of FIG. 7 detect pupil diameter and pupillary reactivity under varying light conditions, allowing for automated assessments of alertness or emotional state. These readings may be used to personalize AR content delivery—for example, increasing information density or highlighting relevant objects based on inferred attention levels. Such passive physiological measurement, when integrated with contextual AR rendering, supports adaptive display logic akin to emerging commercial headsets capable of environment-personalized augmentation.

In one embodiment, the smart eyewear system may further comprise one or more biometric sensors configured to monitor the wearer's vital signs in real-time. Referring to FIG. 7 and FIG. 8, the eyewear may include embedded sensors in the temple regions, bridge, or nose pads to noninvasively detect cardiovascular signals such as heart rate, pulse waveform, and estimated blood pressure. Alternatively, the eyewear may establish a wireless communication link via the Wi-Fi or short-range radio module 760 with one or more peripheral wearable devices—such as a wrist-worn watch, fitness band, or smart ring—capable of transmitting biometric data. In such an embodiment, the digital processor 720 receives synchronized input from these external devices and integrates the physiological data with other contextual modules, enabling dynamic adjustment of AR visualizations or alerts based on the user's physical state. For example, during elevated heart rate or increased sympathetic nervous system response, visual or audio prompts may be selectively suppressed or delayed to avoid cognitive overload.

FIG. 17 illustrates an embodiment of a pupillary movement tracking system implemented within the augmented reality eyewear platform. The system employs digitally predetermined grid coordinates 1700 generated by onboard processors to monitor and quantify the real-time spatial position of the user's pupil. As the pupil moves across this virtual coordinate grid, the system logs the position at discrete time intervals, allowing it to calculate the velocity and trajectory of each movement based on the time elapsed between positional changes 1710. The system includes three outward-facing cameras 120, 124, and 128 and FIG. 17 shows two of those cameras 124 and 128.

These temporal and spatial measurements are used to assess neurological and cognitive metrics, including the user's level of alertness. For instance, erratic, rapid, or inconsistent pupillary movements 1720 may indicate decreased attentional capacity or onset of fatigue, which is an especially important parameter for users engaged in high-risk activities such as driving or operating machinery.

The captured movement data can be formatted into both tabular and graphical outputs 1730 for later clinical review. One such graphic output, shown as display 1740, plots pupil position over time to reveal trends, anomalies, or correlations that may assist a medical professional in diagnosing cognitive, neurological, or ocular conditions.

The system includes an adaptive analytics module that compares the user's live pupillary behavior against customized baseline thresholds. These thresholds are derived from the user's historical data collected during periods of verified wakefulness and full cognitive alertness. Unlike static norms based on population averages, the use of individualized baselines improves diagnostic sensitivity by accounting for physiological differences such as circadian rhythm, sleep habits, occupational demands, and geographic location. For example, a person living in extreme northern latitudes with seasonal daylight extremes may exhibit different pupillary behavior than a person living near the equator. By adjusting for these variables, the system delivers more accurate assessments of situational awareness and fatigue risk in real time.

Figure 18:
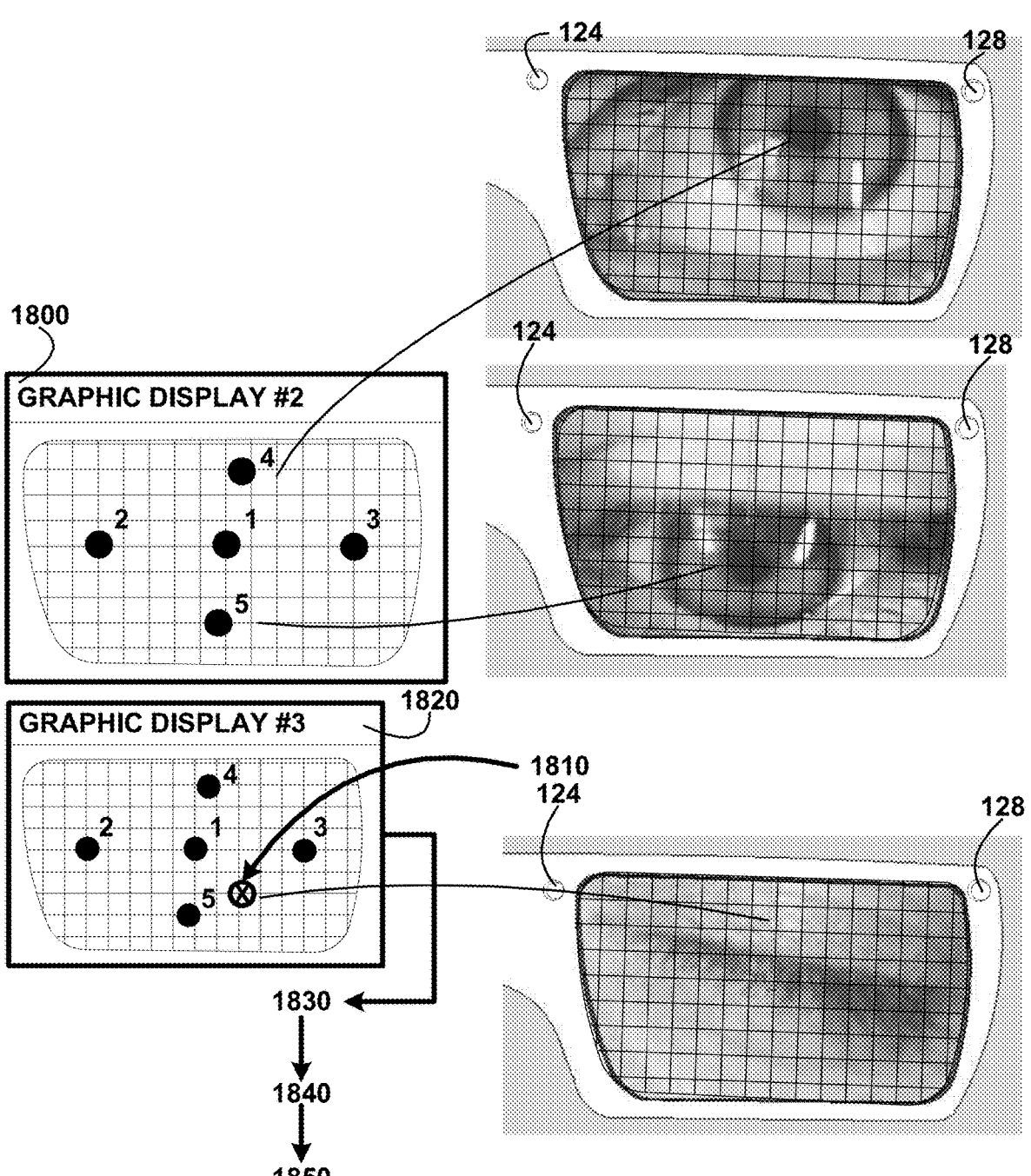
FIG. 18 shows for illustrative purposes only an example of pupillary movement drowsiness determination of one embodiment.

FIG. 18 illustrates an embodiment of the augmented reality eyewear system configured to assess user drowsiness based on real-time analysis of pupillary movement and eyelid behavior. The figure includes a continued biometric plot, referred to as graphic display 1800, showing tracked pupil positions over time. When the system detects that the pupil is no longer visible in the captured image data—due to occlusion by closed eyelids or loss of ocular contrast—it infers that the user's eyes are shut. This condition initiates a first-stage drowsiness alert 1810. The system includes three outward-facing cameras 120, 124, and 128 and FIG. 18 shows two of those cameras 124 and 128.

The system further analyzes the duration and frequency of eyelid closures over a defined observation window. If the eyelid remains closed beyond the user-specific baseline blink duration, or if the blink frequency exhibits irregular patterns, the system elevates its alert state to a second-stage drowsiness condition 1830. Upon entering this second stage, the eyewear activates a preliminary alert protocol 1840, which may include auditory, visual, or haptic warnings designed to prompt user re-engagement.

Graphic display 1820 presents a visualization of blink event tracking and illustrates a third-stage condition—characterized by continued non-responsiveness and absence of voluntary eye opening. If the system detects sustained eyelid closure beyond the defined recovery interval, it triggers an escalation protocol. At this stage, the eyewear may issue critical alerts not only to the user but also to designated emergency contacts, vehicle automation systems, or public safety authorities. The third-stage condition activates override modules 1850, which may include automatic vehicle pull-over assistance, communication dispatch, or location-based intervention services. This multi-tiered drowsiness detection architecture enables early detection and intervention in fatigue-related scenarios, enhancing user safety through biometric vigilance and intelligent response mechanisms.

FIG. 19 illustrates an embodiment of the augmented reality eyewear system incorporating real-time interaction with an artificial intelligence (AI) application and augmented visual projection of contextual information. The user wearing the smart eyewear glasses shown previously in FIG. 1, is traveling along a roadway 1900. The system includes three outward-facing cameras 120, 124, and 128, which provide overlapping fields of view 122, 126, and 130, respectively, to capture the surrounding environment.

In this scenario, the user initiates an inquiry by speaking a verbal command into the system's audio input module, asking, "AI chat, how far to the next EV recharging station?" The spoken query is converted to text using an onboard or cloud-based speech recognition engine and is optionally projected onto the left lens as visual confirmation to the user.

The AI module, whether embedded locally or running on a connected remote server, processes the inquiry using geolocation data, known EV charging infrastructure maps, and real-time user positioning. The system generates a contextual response such as, "The next EV recharging station is 47 miles away at a convenience store on the west side of the road" 1920. This information is then rendered onto the right lens as an augmented text overlay, allowing the user to receive the response without diverting attention from the road.

In another embodiment, the AI response is delivered audibly via the frame-integrated audio alert speaker module 1010 of FIG. 10A, enabling hands-free feedback. In addition, a complementary AR application projects a digital image 1930 of the identified convenience store 1940 onto the right lens. This image may include visual cues such as directional arrows, estimated arrival time, or branding elements associated with the charging location, enhancing the user's situational awareness and navigation experience without requiring manual input or external displays.

Referring again to FIG. 4 and FIG. 7, the system may allow the user to verbally interact with a local AI module 784 while simultaneously presenting visual AR overlays based on AI outputs. For instance, in one embodiment as an example use case, while attending a live sporting event, the user may gaze at a particular player or field section and query, via microphone 782, "Who is that?" or "What's their current stat line?" The AI module may identify the queried subject using camera input and facial or object recognition 432, then retrieve and project current data (e.g., name, number, performance stats) onto the lens. This data may be accompanied by an audio summary via speaker 786. The combination of gaze-aware input, real-time AI analysis, and synchronized AR projection allows highly immersive, hands-free, situational data retrieval, closely mirroring functionalities attributed to current-generation AR wearables developed by large commercial entities.

Figure 20:
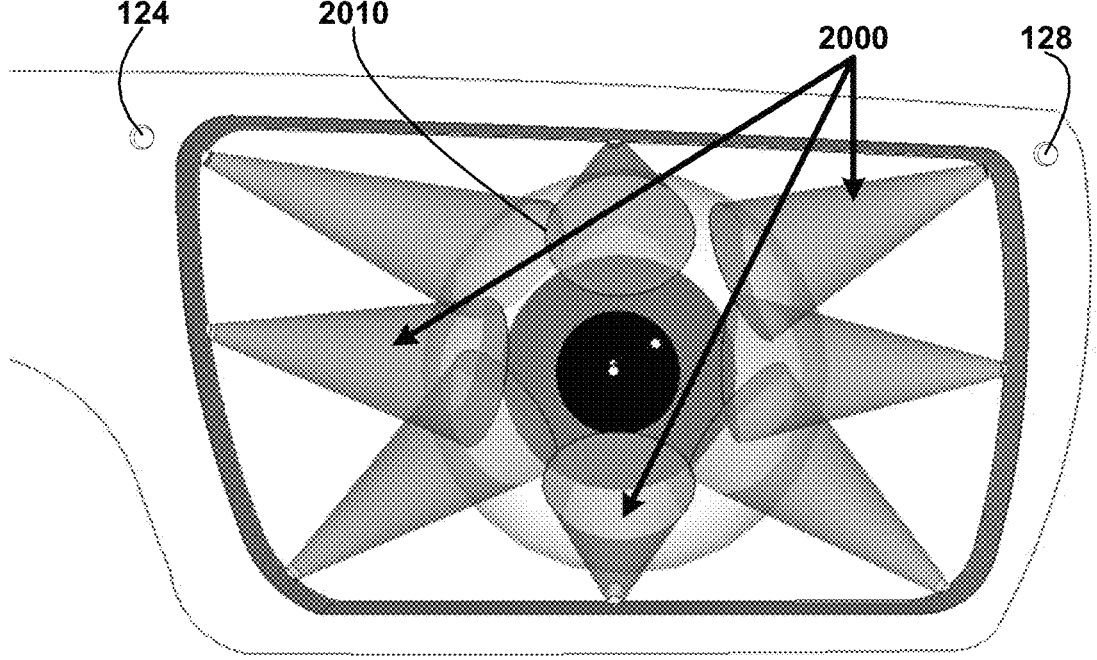
FIG. 20 shows for illustrative purposes only an example of the frame camera field of view of one embodiment.

FIG. 20 illustrates an embodiment of the augmented reality eyewear system configured with frame-embedded cameras positioned to monitor the user's eye region. The diagram shows the focal length and field of view 2000 of the inward-facing frame cameras, which are installed along the inside perimeter of the eyewear frame. These cameras are optically aligned to capture high-resolution images of the user's iris and pupil while maintaining full visibility during forward gaze. The camera fields of view are arranged to partially overlap 2010 in the central region of the eye, ensuring redundant coverage and compensating for minor misalignments or head motion. This overlapping configuration allows for improved accuracy in eye tracking and biometric imaging by providing multi-angle perspectives on critical ocular landmarks. The system includes three outward-facing cameras 120, 124, and 128 and FIG. 20 shows two of those cameras 124 and 128.

Figure 21:
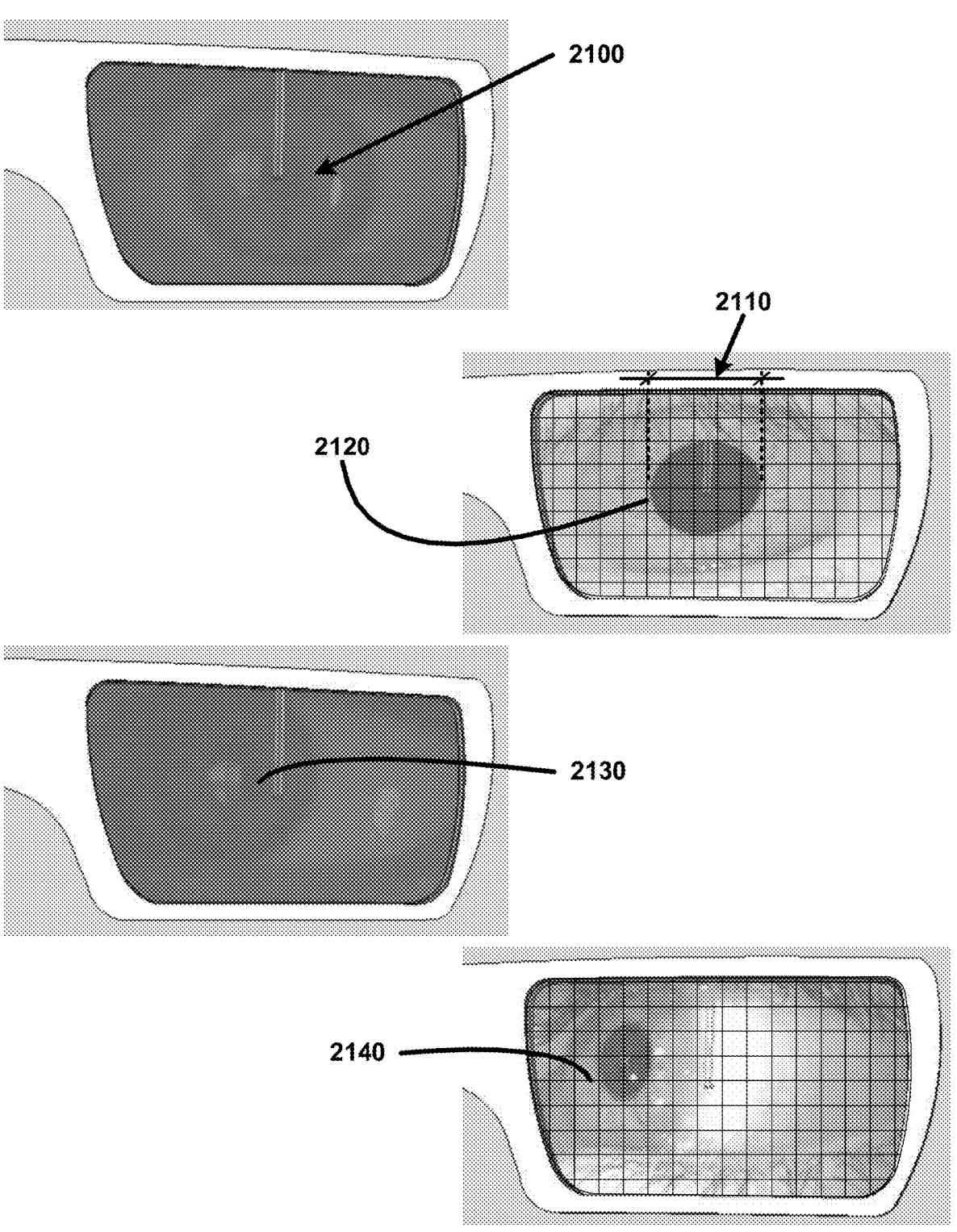
FIG. 21 shows for illustrative purposes only an example of pupil measurement in low light of one embodiment.

FIG. 21 depicts an embodiment of a low-light pupil measurement system using infrared imaging. In conditions of insufficient ambient illumination, the standard visible-light camera lens field of view 2100 embedded in the eyewear lens may be unable to generate a clear contrast image of the pupil. To address this, the system automatically switches to an infrared imaging mode. Incoming image data is processed through an infrared detection module that enhances contrast between ocular features and the surrounding tissue 2120.

Using this infrared-filtered image, the system identifies the boundary of the pupil and measures its diameter 2110 by applying a set of predetermined grid coordinates calibrated to the contrasting edge positions. This method ensures consistent measurement of pupil size, even in dark environments. In cases where visible-light imaging from the frame-mounted camera 2130 fails to produce adequate contrast, the system compensates by relying exclusively on the infrared signal pathway to generate a high-resolution, contrast-enhanced image. The resulting pupil size measurement 2140 supports real-time analysis of cognitive load, user alertness, or neurological response, regardless of external lighting conditions.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the embodiments as defined by the following claims.

What is claimed is:

1. A wearable augmented reality eyewear system, comprising:

a frame having at least one transparent lens and configured to be worn by a user and adjacent to the user's eyes;

at least one outward-facing camera coupled to at least one of the frame or the transparent lens, and configured to capture live multimedia images of objects that are visually present by the user within a field of vision through the at least one transparent lens;

at least one inward-facing camera coupled to at least one of the frame or the transparent lenses configured to detect movement, dilation and gaze direction of the pupil;

an object recognition processor coupled to a remote database and the at least one outward-facing camera and configured to receive in real-time the captured live multimedia images of the objects and compare the captured live multimedia images of the objects to information of known objects in the database to automatically recognize and identify the objects and gather information about the recognized and identified objects;

a pupillary movements tracking system coupled to the at least one inward-facing camera and configured to interact with the pupil movements of the user's eye and use the movement, dilation and gaze direction of the pupil to track at least one object in the user's field of vision that the user is looking at;

wherein the object recognition processor is further configured to determine a gaze vector based on detected pupil position relative to a virtual coordinate grid, to identify a region of the captured live multimedia images within the user's field of view corresponding to the gaze vector, and to perform object recognition processing on the identified region;

wherein the object recognition processor is further configured to detect a hand gesture performed by the user within the field of view of the at least one outward-facing camera and control object recognition processing of the captured live multimedia images in response to the detected hand gesture;

a projector wirelessly coupled to the object recognition processor and the pupillary movements tracking system and configured to project to the user via the at least one transparent lens readable information associated with the gathered information about the recognized and identified objects; and a speaker coupled to the frame, the object recognition processor and the pupillary movements tracking system and configured to transmit audio information associated with the gathered information about the recognized and identified objects.

2. The wearable augmented reality eyewear system of claim 1, further comprising a microphone coupled to the frame and configured to receive user voice commands to initiate system functions.

3. The wearable augmented reality eyewear system of claim 2, further comprising an artificial intelligence application wirelessly coupled to the microphone and configured to translate in real-time foreign languages detected by the microphone and transmitting the translations to the speaker and displaying the translations on the at least one transparent lens.

4. The wearable augmented reality eyewear system of claim 1, wherein the projector is further configured to display targeted advertising content based on the gathered information about the recognized and identified objects.

5. The wearable augmented reality eyewear system of claim 1, further comprising a plurality of outward-facing cameras having overlapping fields of view and configured to capture stereoscopic images of the live multimedia images of the objects to create spatial depth estimation of the objects.

6. The wearable augmented reality eyewear system of claim 1, wherein the tracked movement, dilation and gaze direction of the pupil is analyzed and used to display contextual content associated with the object when pupil dilation and gaze fixation exceed predefined thresholds, indicating user interest.

7. The wearable augmented reality eyewear system of claim 1, further comprising a facial recognition module coupled to the object recognition processor and configured to identify individuals in the field of view of the user based on the gathered information about the recognized and identified objects.

8. A wearable augmented reality eyewear system, comprising:

a frame having at least one transparent lens and configured to be worn by a user and adjacent to the user's eyes;

a plurality of outward-facing cameras coupled to at least one of the frame or the transparent lens, and configured to capture live multimedia images of objects that are visually present by the user within a field of vision through the at least one transparent lens;

at least one inward-facing camera coupled to at least one of the frame or the transparent lenses configured to detect movement, dilation and gaze direction of the pupil;

a gesture recognition system coupled to at least one inward-facing camera configured to interpret blinking patterns and eye glances;

an object recognition processor coupled to a remote database and the plurality of outward-facing cameras and configured to receive in real-time the captured live multimedia images of the objects and compare the captured live multimedia images of the objects to information of known objects in the database to automatically recognize and identify the objects and gather information about the recognized and identified objects;

a pupillary movements tracking system coupled to the at least one inward-facing camera and configured to interact with the pupil movements of the user's eye and use the movement, dilation and gaze direction of the pupil to track at least one object in the user's field of vision that the user is looking at;

wherein the object recognition processor is further configured to determine a gaze vector based on detected pupil position relative to a virtual coordinate grid, to identify a region of the captured live multimedia images within the user's field of view corresponding to the gaze vector, and to perform object recognition processing on the identified region when gaze fixation exceeds a predefined duration threshold indicating intentional observation by the user;

wherein the object recognition processor is further configured to detect a hand gesture performed by the user within the field of view of the at least one outward-facing camera and control object recognition processing of the captured live multimedia images in response to the detected hand gesture;

a projector wirelessly coupled to the object recognition processor and the pupillary movements tracking system and configured to project to the user via the at least one transparent lens readable information associated with the gathered information about the recognized and identified objects; and a speaker coupled to the frame, the object recognition processor and the pupillary movements tracking system and configured to transmit audio information associated with the gathered information about the recognized and identified objects.

9. The wearable augmented reality eyewear system of claim 8, further comprising a microphone coupled to the frame and configured to receive user voice commands to initiate system functions.

10. The wearable augmented reality eyewear system of claim 9, further comprising an artificial intelligence application wirelessly coupled to the microphone and configured to translate in real-time foreign languages detected by the microphone and transmitting the translations to the speaker and displaying the translations on the at least one transparent lens.

11. The wearable augmented reality eyewear system of claim 8, wherein the projector is further configured to display targeted advertising content based on the gathered information about the recognized and identified objects.

12. The wearable augmented reality eyewear system of claim 8, further comprising a plurality of outward-facing cameras having overlapping fields of view and configured to capture stereoscopic images of the live multimedia images of the objects to create spatial depth estimation of the objects.

13. The wearable augmented reality eyewear system of claim 8, wherein the tracked movement, dilation and gaze direction of the pupil is analyzed and used to display contextual content associated with the object when pupil dilation and gaze fixation exceed predefined thresholds, indicating user interest.

14. The wearable augmented reality eyewear system of claim 8, further comprising a facial recognition module coupled to the object recognition processor and configured to identify individuals in the field of view of the user based on the gathered information about the recognized and identified objects.

15. A wearable augmented reality eyewear system, comprising:

a frame having at least one transparent lens and configured to be worn by a user and adjacent to the user's eyes;

a plurality of outward-facing cameras coupled to at least one of the frame or the transparent lens, and configured to capture live multimedia images of objects that are visually present by the user within a field of vision through the at least one transparent lens;

at least one inward-facing camera coupled to at least one of the frame or the transparent lenses configured to detect movement, dilation and gaze direction of the pupil;

a gesture recognition system coupled to at least one inward-facing camera configured to interpret blinking patterns and eye glances;

a location module configured to track a real-time geographical location of the user;

an object recognition processor coupled to a remote database and the at least one camera and configured to receive in real-time the captured live multimedia images of the objects and compare the captured live multimedia images of the objects to information of known objects in the database that are associated with the real-time geographical location of the user to automatically recognize and identify the objects and gather information about the recognized and identified objects;

a pupillary movements tracking system coupled to the at least one inward-facing camera and configured to interact with the pupil movements of the user's eye and use the movement, dilation and gaze direction of the pupil to track at least one object in the user's field of vision that the user is looking at;

wherein the object recognition processor is further configured to determine a gaze vector based on detected pupil position relative to a virtual coordinate grid corresponding to the at least one transparent lens, to identify a region of the captured live multimedia images within the user's field of view corresponding to the gaze vector, and to perform object recognition processing on the identified region when gaze fixation exceeds a predefined duration threshold indicating intentional observation by the user;

wherein the object recognition processor is further configured to detect a hand gesture performed by the user within the field of view of the at least one outward-facing camera and control object recognition processing of the captured live multimedia images in response to the detected hand gesture;

a projector wirelessly coupled to the object recognition processor and the pupillary movements tracking system and configured to project to the user via the at least one transparent lens readable information associated with the gathered information about the recognized and identified objects; and a speaker coupled to the frame, the object recognition processor and the pupillary movements tracking system and configured to transmit audio information associated with the gathered information about the recognized and identified objects.

16. The wearable augmented reality eyewear system of claim 15, further comprising a microphone coupled to the frame and configured to receive user voice commands to initiate system functions.

17. The wearable augmented reality eyewear system of claim 16, further comprising an artificial intelligence application wirelessly coupled to the microphone and configured to translate in real-time foreign languages detected by the microphone and transmitting the translations to the speaker and displaying the translations on the at least one transparent lens.

18. The wearable augmented reality eyewear system of claim 15, wherein the projector is further configured to display targeted advertising content based on the gathered information about the recognized and identified objects.

19. The wearable augmented reality eyewear system of claim 15, wherein the tracked movement, dilation and gaze direction of the pupil is analyzed and used to display contextual content associated with the object when pupil dilation and gaze fixation exceed predefined thresholds, indicating user interest.

20. The wearable augmented reality eyewear system of claim 15, further comprising a facial recognition module coupled to the object recognition processor and configured to identify individuals in the field of view of the user based on the gathered information about the recognized and identified objects.

* * * * *